US012558470B2

(12) United States Patent
Lerner

(10) Patent No.: US 12,558,470 B2
(45) Date of Patent: Feb. 24, 2026

(54) GUIDED BLOOD FILTRATION THERAPY, SYSTEMS, AND METHODS

(71) Applicant: CorRen Medical, Inc., Minneapolis, MN (US)

(72) Inventor: David Lerner, St. Paul, MN (US)

(73) Assignee: CorRen Medical, Inc., Minneapolis, MN (US)

( * ) Notice: Subject to any disclaimer, the term of this patent is extended or adjusted under 35 U.S.C. 154(b) by 418 days.

(21) Appl. No.: 18/259,980

(22) PCT Filed: Dec. 30, 2021

(86) PCT No.: PCT/US2021/073205
§ 371 (c)(1),
(2) Date: Jun. 29, 2023

(87) PCT Pub. No.: WO2022/147482
PCT Pub. Date: Jul. 7, 2022

(65) Prior Publication Data
US 2024/0066199 A1 Feb. 29, 2024

Related U.S. Application Data

(60) Provisional application No. 63/199,485, filed on Dec. 31, 2020.

(51) Int. Cl.
A61M 1/34 (2006.01)
G16H 20/40 (2018.01)

(52) U.S. Cl.
CPC .......... A61M 1/3403 (2014.02); G16H 20/40 (2018.01); *A61M 2202/0413* (2013.01);
(Continued)

(58) Field of Classification Search
CPC ........ A61M 1/3403; A61M 2202/0413; A61M 2205/3303; A61M 2205/502;
(Continued)

(56) References Cited

U.S. PATENT DOCUMENTS 5,178,154 A 1/1993 Ackmann et al.
5,511,553 A 4/1996 Segalowitz
(Continued)

FOREIGN PATENT DOCUMENTS

CN 209826715 U 12/2019
DE 102017130548 A1 6/2019
(Continued)

OTHER PUBLICATIONS

"International Application Serial No. PCT/US2021/073205, International Search Report mailed Jun. 3, 2022", 5 pgs.
(Continued)

*Primary Examiner* — Andrew J Mensh
(74) *Attorney, Agent, or Firm* — Schwegman Lundberg & Woessner, P.A.

(57) ABSTRACT
A blood filtration system may include one or more sensors. The sensors may determine physiological parameters, for instance one or more of venous oxygen saturation (SvO2) or hematocrit of a patient. The blood filtration system may include a controller. The controller may communicate with the one or more sensors. The controller may monitor the physiological parameters using the sensors. The controller may include a display module that generates content. A display may present the content. The content may include a diagnostic matrix having a diagnostic point. The display module may change the diagnostic point within the diagnostic matrix according to changes in the monitored physiological parameters.

23 Claims, 15 Drawing Sheets

(52) U.S. Cl.
    CPC ............... *A61M 2205/3303* (2013.01); *A61M 2205/502* (2013.01); *A61M 2230/005* (2013.01); *A61M 2230/04* (2013.01); *A61M 2230/207* (2013.01); *A61M 2230/42* (2013.01); *A61M 2230/46* (2013.01)

(58) Field of Classification Search
    CPC ........ A61M 2230/005; A61M 2230/04; A61M 2230/207; A61M 2230/42; A61M 2230/46; G16H 20/40
    USPC .......................................................... 604/5.01
    See application file for complete search history.

(56)                    References Cited

U.S. PATENT DOCUMENTS

| | | | | | |
|---|---|---|---|---|---|
| 5,928,180 | A | * | 7/1999 | Krivitski | A61M 1/16 |
| | | | | | 210/85 |
| 6,610,024 | B1 | * | 8/2003 | Benatti | A61M 1/28 |
| | | | | | 604/4.01 |
| 7,788,038 | B2 | * | 8/2010 | Oshita | G16H 40/67 |
| | | | | | 604/4.01 |
| 8,000,779 | B2 | | 8/2011 | Bartnik et al. | |
| 8,473,041 | B2 | * | 6/2013 | Bartnik | A61B 5/02028 |
| | | | | | 600/513 |
| 2014/0118166 | A1 | * | 5/2014 | Hampapuram | G16H 50/30 |
| | | | | | 340/870.16 |

FOREIGN PATENT DOCUMENTS

| | | | | |
|---|---|---|---|---|
| JP | | 2012254251 | A * | 12/2012 |
| KR | | 20120120262 | A | 11/2012 |
| WO | WO-2008029396 | A2 | | 3/2008 |
| WO | WO-2017139839 | A1 | | 8/2017 |
| WO | WO-2018202661 | A1 | | 11/2018 |
| WO | WO-2020061619 | A1 | | 4/2020 |
| WO | WO-2022147482 | A1 | | 7/2022 |

OTHER PUBLICATIONS

"International Application Serial No. PCT/US2021/073205, Invitation to Pay Additional Fees mailed Mar. 14, 2022", 2 pgs.
"International Application Serial No. PCT/US2021/073205, Written Opinion mailed Jun. 3, 2022", 9 pgs.

* cited by examiner

1900

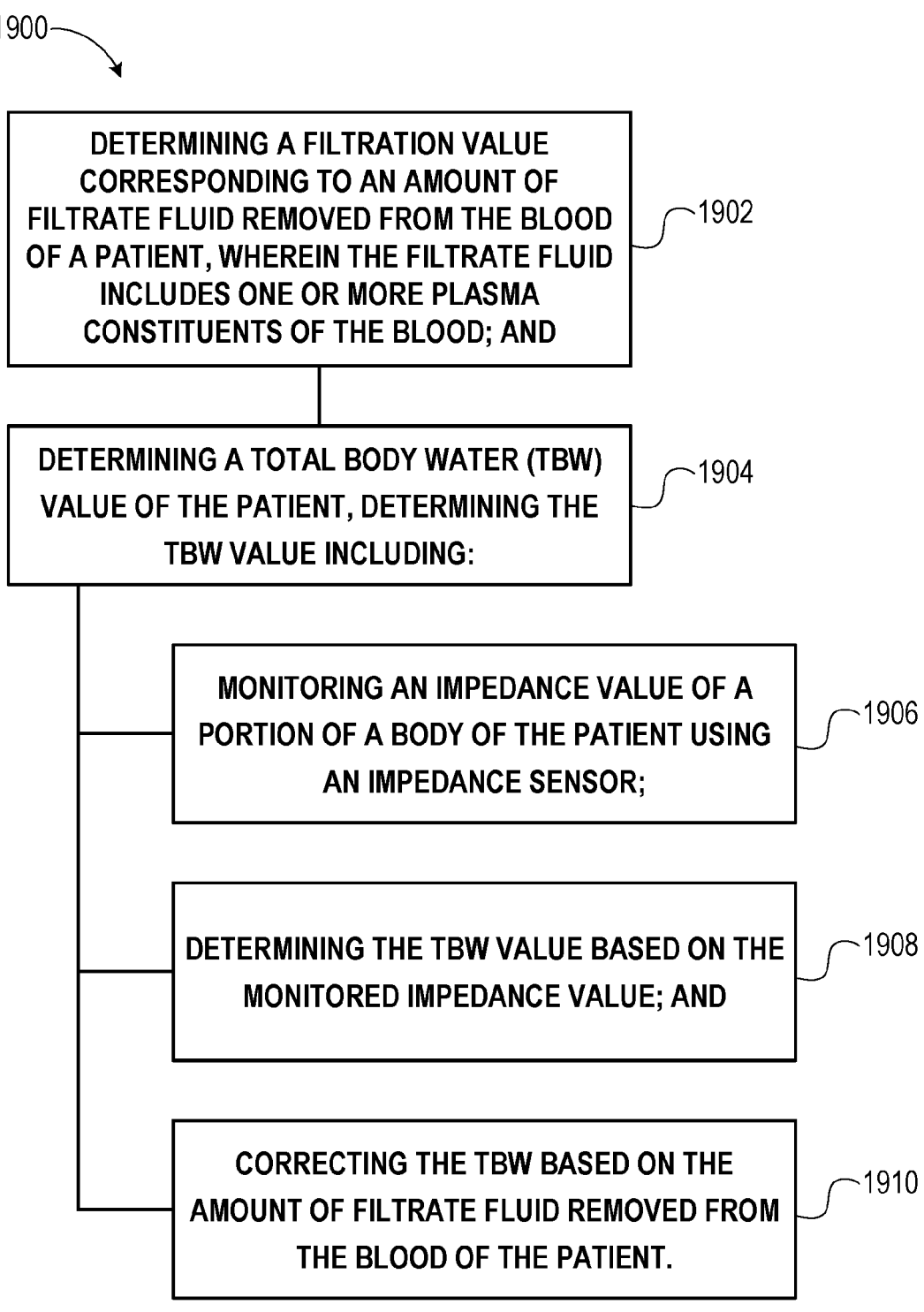

DETERMINING A FILTRATION VALUE CORRESPONDING TO AN AMOUNT OF FILTRATE FLUID REMOVED FROM THE BLOOD OF A PATIENT, WHEREIN THE FILTRATE FLUID INCLUDES ONE OR MORE PLASMA CONSTITUENTS OF THE BLOOD; AND — 1902

DETERMINING A TOTAL BODY WATER (TBW) VALUE OF THE PATIENT, DETERMINING THE TBW VALUE INCLUDING: — 1904

MONITORING AN IMPEDANCE VALUE OF A PORTION OF A BODY OF THE PATIENT USING AN IMPEDANCE SENSOR; — 1906

DETERMINING THE TBW VALUE BASED ON THE MONITORED IMPEDANCE VALUE; AND — 1908

CORRECTING THE TBW BASED ON THE AMOUNT OF FILTRATE FLUID REMOVED FROM THE BLOOD OF THE PATIENT. — 1910

FIG. 19

GUIDED BLOOD FILTRATION THERAPY, SYSTEMS, AND METHODS

CLAIM FOR PRIORITY

This application is a U.S. national stage filing under 35 U.S.C. § 371 from International Application No. PCT/US2021/073205, filed on Dec. 30, 2021, and published as WO 2022/147482 on Jul. 7, 2022, which claims the benefit of priority of U.S. Application Ser. No. 63/199,485, filed Dec. 31, 2020, the benefit of priority of each of which is claimed herein, and which applications and publication are hereby incorporated herein by reference in its their entirety.

TECHNICAL FIELD

This document pertains generally, but not by way of limitation, to a blood filtration system for removing one or more plasma constituents from blood of a patient.

BACKGROUND

In many disease states and other clinical circumstances, patients can become overloaded with blood volume (e.g., hypervolemia, or the like). For instance, a patient can experience so-called third-spacing (e.g., blood plasma translocating into the interstitial tissue, or the like). In another example, the patient can experience a low blood volume (e.g., hypovolemia, or the like). These states may lead to serious health risks for a patient. In yet another example, renal disease, heart disease, liver disease, severe burns, or many other pathological states can lead to a loss or gain of fluid by a patient. The patient may undergo therapy to remove the fluid, for example using extracorporeal ultrafiltration to remove the fluid from the blood of a patient. In still yet another example, a patient can be infused with fluid prior to a procedure, and then require subsequent removal of that fluid after the procedure. Unlike pharmacological therapy with diuretics, ultrafiltration is fast, precise, and does not place a strain on the kidneys.

Blood filtration systems are known for removal of blood from the venous circulation of the patient and separates plasma water and electrolytes from erythrocytes (e.g., red blood cells, or the like) and other blood constituents by means of, for example, a single use, disposable filter. After filtration, some of the plasma water is conveyed to a bag for disposal. The balance of the plasma water, the erythrocytes, and other blood constituents are returned to the patient's venous circulation. Note that as plasma water (e.g., ultrafiltrate, or the like) is removed from the circulatory system via ultrafiltration and fluid that is located in the interstitial space (e.g., one or more of tissue fluid, edema, congestion, or the like) can be recruited back into the circulatory system according to starling forces. In other words, as plasma fluid is removed from the circulatory system, additional fluid may diffuse from the tissues back into the circulatory system thus compensating, in whole or in part, for the fluid removed via ultrafiltration. The rate at which fluid flows back into the circulatory system is known as a plasma refill rate ("PRR"). The PRR depends on multiple factors including (but not limited to) plasma oncotic pressure, plasma hydrostatic pressure, interstitial osmotic pressure, interstitial hydrostatic pressure, and pressure derived from skin turgidity, elasticity, or the like. Accordingly, the plasma refill rate can vary from patient to patient, or in one patient as therapy proceeds.

In some approaches, the ultrafiltration rate (UFR) exceeds the PRR. Accordingly, in this approach, too much plasma fluid may be removed from the circulatory system. For instance, the plasma fluid may be removed too quickly or too much plasma fluid may be removed from the patient an absolute sense. Thus, the blood of the patient may become hemoconcentrated (e.g., due to excessive rise in hematocrit, or the like). Hemoconcentration of the blood may increase the viscosity of the blood. As a result, hemoconcentrated blood may increase the likelihood of clotting in the filter of the blood filtration system. Further, if plasma volume is reduced to a low enough level, one or more of blood pressure or tissue perfusion may become inadequate to sustain life of the patient.

SUMMARY

The present inventors have recognized, among other things, that a problem to be solved can include maintaining one or more of cardiovascular stability, hemodynamic stability, or pulmonary stability of a patient. For example, the removal of filtrate fluid from blood of a patient may increase the hematocrit value of the blood of the patient. Accordingly, the blood of the patient may become hemoconcentrated. Hemoconcentration of blood may affect one or more of the cardiovascular stability, hemodynamic stability, or pulmonary stability of the patient. In another example, the venous oxygen saturation ("SvO2") of the patient may change as filtrate fluid is removed from the blood of the patient.

In yet another example, the present inventors have recognized, among other things, that a problem to be solved can include determining one or more physiological parameters of a patient. For instance, the physiological parameters of the patient may include one or more of the hematocrit value, SvO2, relative blood volume, absolute blood volume, plasma volume, oxygen extraction ratio, stroke volume, carotid flow time, cardiac output, cardiac power, central venous pressure, mean arterial pressure, systemic vascular resistance, heart rate, respiratory rate, cardiac power, thoracic fluid content, or the like. The physiological parameters of a patient may change in correspondence with removal of filtrate fluid from blood of the patient. For example, the systemic vascular resistance of the patient may change in correspondence with one or more of viscosity of blood (e.g., hemoconcentration, or the like) or vessel geometry (e.g., expansion or constriction of blood vessels in correspondence with the plasma volume of the patient, or the like).

The present subject matter can help provide a solution to one or more of these problems, such as with a blood filtration system. The blood filtration system may include one or more sensors configured to determine one or more physiological parameters including (but not limited to) venous oxygen saturation and hematocrit of a patient. The blood filtration system may include a controller in communication with the one or more sensors. The controller may monitor the physiological parameters using the sensors. The controller may include a display module configured to generate content. In an example, the blood filtration system may include a display. The display may present the content, for example a diagnostic matrix having a diagnostic point. In another example, display module may cooperate with the display to move the diagnostic point within the diagnostic matrix. For example, the display module may move the diagnostic point in correspondence with changes in the monitored physiological parameters.

In an example, the diagnostic matrix may include one or more axis. The one or more axis may be associated with the monitored physiological parameters. The one or more axis may have a plurality of values corresponding with values of the monitored physiological parameters included along the axis. For instance, the diagnostic matrix may include hematocrit values of a patient along a first axis. The diagnostic matrix may include SvO2 values along a second axis. Accordingly, the values of the monitored physiological parameters may be incremented along axis associated with the monitored physiological parameters.

The diagnostic point may change with respect to the diagnostic matrix. For example, the diagnostic point may move along the first axis in correspondence with changes in hematocrit values of the patient. For instance, the system may determine the patient has a first hematocrit value. The diagnostic point may be in a first location along the first axis in correspondence with the first hematocrit value. The system may determine the patient has a second hematocrit value. The diagnostic point may be in a second location along the first axis in correspondence with the second hematocrit value. The diagnostic point may move along the second axis in correspondence with changes in the ScO2. In another example, the diagnostic matrix includes a third axis. The diagnostic matrix may include relative blood volume values along the third axis. The diagnostic point may move along the third axis in correspondence with changes in relative blood volume of the patient. Accordingly, the diagnostic matrix may be multi-dimensional. The diagnostic point may move within the diagnostic matrix in correspondence with changes in the monitored physiological parameters.

In yet another example, the diagnostic point may change in correspondence with changes in the monitored physiological parameters. For instance, a size of the diagnostic point may change in correspondence with changes in the monitored physiological parameters. For instance, the diagnostic point may change in size with respect to (e.g., within, in relation to, or the like) the diagnostic matrix. In another example, a color of the diagnostic point may change in correspondence with changes in the monitored physiological parameters. Thus, the diagnostic point may change in correspondence with changes in the monitored physiological parameters.

In still yet another example, the content presented by the system includes a zone of stability. For instance, the zone of stability may be presented with the diagnostic matrix on the display. The diagnostic point may change with respect to the zone of stability. For instance, the diagnostic point may move with respect to the zone of stability.

The zone of stability may include a range (e.g., subset, subgroup, division, section, portion, or the like) of values within the values of physiological parameters included in the diagnostic matrix. In an example, the first axis may include values of hematocrit between 30 percent and 60 percent. The zone of stability may include a range within the hematocrit values. For instance, the zone of stability may include a range of hematocrit values between 45 percent and 55 percent. In some examples, the zone of stability is user-configurable. For instance, a healthcare provider may set the range of values for the zone of stability.

The diagnostic matrix may facilitate maintenance of physiological stability of a patient. For instance, the diagnostic matrix may facilitate maintenance of one or more of cardiovascular stability, hemodynamic stability, or pulmonary stability of a patient. For example, the location of the diagnostic point within the diagnostic matrix may allow a user (e.g., healthcare provider, technician, or the like) to observe the monitored physiological parameters of the patient. The user may observe one or more of the location, trend, movement, size, shape, color, or the like—of the diagnostic point relative to the diagnostic matrix. In another example, the user may observe the diagnostic point relative to the zone of stability. In an example, the user may adjust operation of the blood filtration system based on observation of the diagnostic point relative to the diagnostic matrix (or the zone of stability). For instance, the user may adjust a filtration rate of the blood filtration system based on observation of the diagnostic point relative to the diagnostic matrix. The filtration rate may correspond with a rate of removal of filtrate fluid from the blood of the patient. In another example, the user may increase the filtration rate in correspondence with the hematocrit being within the zone of stability. In yet another example, the user may decrease the filtration rate in correspondence with the hematocrit outside the zone of stability. Accordingly, the blood filtration system may remove fluid from a patient and maintain one or more of cardiovascular stability, hemodynamic stability, or pulmonary stability of the patient.

In another example, the blood filtration system may determine one or of the physiological parameters of a patient. For instance, the blood filtration system may determine physiological parameters using an impedance sensor. The impedance sensor may communicate with a body of the patient. For instance, the impedance sensor may communicate with the body to determine an impedance of the body. The blood filtration system may use the impedance of the body to determine the physiological parameters of the body. For instance, the physiological parameters may change in correspondence with changes in the impedance of the body. In another example, the impedance sensor may communicate with a thorax of the patient. Accordingly, the impedance sensor may determine an impedance of the thorax of the patient. In another example, the blood filtration system uses one or more of impedance cardiography, impedance pneumology, or the like to determine the physiological parameters. For instance, the impedance sensor may use one or more electrodes to determine pulmonary fluid content. In yet another example, the impedance sensor uses the one or more electrodes to determine cardiac functions of the patient, including (but not limited to) cardiac output, cardiac power, ejection time, stroke volume, or the like. Thus, the blood filtration system may use the impedance sensor to determine the impedance of the body (and physiological parameters associated with the impedance of the body).

As described herein, the blood filtration system may monitor one or more physiological parameters of a patient. In an example, the blood filtration system may monitor the impedance sensor. For instance, the controller may communicate with the impedance sensor to monitor one or more of the physiological parameters. The controller may receive impedance values of the body from the impedance sensor. The controller may determine physiological parameters based on the monitored impedance values from the impedance sensor. Accordingly, the blood filtration system may monitor physiological parameters of the patient including (but not limited to) the hematocrit value, SvO2, relative blood volume, absolute blood volume, plasma volume, oxygen extraction ratio, ejection time, stroke volume, carotid flow time, cardiac output, cardiac power, central venous pressure, mean arterial pressure, systemic vascular resistance, heart rate, respiratory rate, cardiac power, thoracic fluid content, or the like.

As described herein, the blood filtration system includes one or more sensors. For instance, blood filtration system may include a pressure sensor that determines pressure in vasculature of the patient. The controller may communicate with the pressure sensor to monitor the pressure in the vasculature of the patient. In an example, the pressure sensor may communicate with one or more of a withdrawal lumen or an infusion lumen of a catheter. The catheter may be inserted into vasculature of the patient. Accordingly, the pressure sensor may determine pressure in vasculature of a patient, including (but not limited to) central venous pressure, mean arterial pressure, jugular venous pulse, or the like. In an example, the system may use the pressure sensor to determine heart sounds of a patient, or the like.

The blood filtration system may use one or more of an invasive sensor or a non-invasive sensor to determine physiological parameters of a patient. In an example, the pressure sensor may be an invasive sensor that communicates with bodily fluids of a patient. For instance, the pressure sensor may communicate with vasculature of a patient. In another example, the hematocrit sensor may be an invasive sensor. For instance, the hematocrit sensor may determine optical characteristics of blood of a patient. The optical characteristics of the blood may correspond with the hematocrit value of the patient. Accordingly, the invasive sensor may communicate with internal portions of the body of the patient (or internal fluids of the patient), for instance by puncturing the skin of the patient (e.g., with a catheter inserted into a vein, or the like). The impedance sensor may be a non-invasive sensor. For example, the impedance sensor may include one or more electrodes secured to a body of a patient. In another example, the electrodes may engage skin of the patient. Thus, the non-invasive sensor may communicate with the body of the patient without puncturing skin of the patient (e.g., by transmitting a signal through the skin, or the like).

In an example, the blood filtration system may determine at least the systemic vascular resistance of a patient using both the invasive sensor and the non-invasive sensor. For instance, the systemic vascular resistance may be based on one or more of mean arterial pressure, central venous pressure, or cardiac output. The blood filtration system may monitor one or more of the central venous pressure or the mean arterial pressure using the pressure sensor (in communication with vasculature of the patient). Monitoring the central venous pressure or the mean arterial pressure may enhance the accuracy of determining the systemic vascular resistance.

In some approaches, the central venous pressure may be estimated in correspondence with systemic vascular resistance determinations. In another approach, the central venous pressure may be determined by a user. The user may input the central venous pressure into the blood filtration system. In this approach, the system may determine the systemic vascular resistance using the user-determined central venous pressure. The blood filtration system may repeatedly determine the central venous pressure of the patient using the pressure sensor. The blood filtration system may determine the systemic vascular resistance based on the repeatedly determined central venous pressure. In another example, the blood filtration system may use the repeatedly determined central venous pressure of the patient to determine the systemic vascular resistance of the patient. In yet another example, the blood filtration system may monitor the cardiac output of the patient using the impedance sensor. Accordingly, accuracy of the systemic vascular resistance determination is enhanced because the blood filtration system monitors the physiological parameters using the invasive sensor and the non-invasive sensor. In an example, the blood filtration system repeatedly determines the systemic vascular resistance based on physiological parameters received from the invasive sensor and the non-invasive sensor. For instance, blood filtration system may monitor changes in the central venous pressure to enhance the accuracy the systemic vascular resistance determined with the blood filtration system. Thus, the blood filtration system enhances accuracy of physiological parameters determinations, for instance because the blood filtration system communicates with the invasive sensor (e.g., the pressure sensor, or the like) and the non-invasive sensor (e.g., the impedance sensor, or the like). Accordingly, the diagnostic matrix may present physiological parameters having enhanced accuracy.

This overview is intended to provide an overview of subject matter of the present patent application. This overview is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 19 shows one example of a method for operating a blood filtration system.

DETAILED DESCRIPTION

Figure 1:
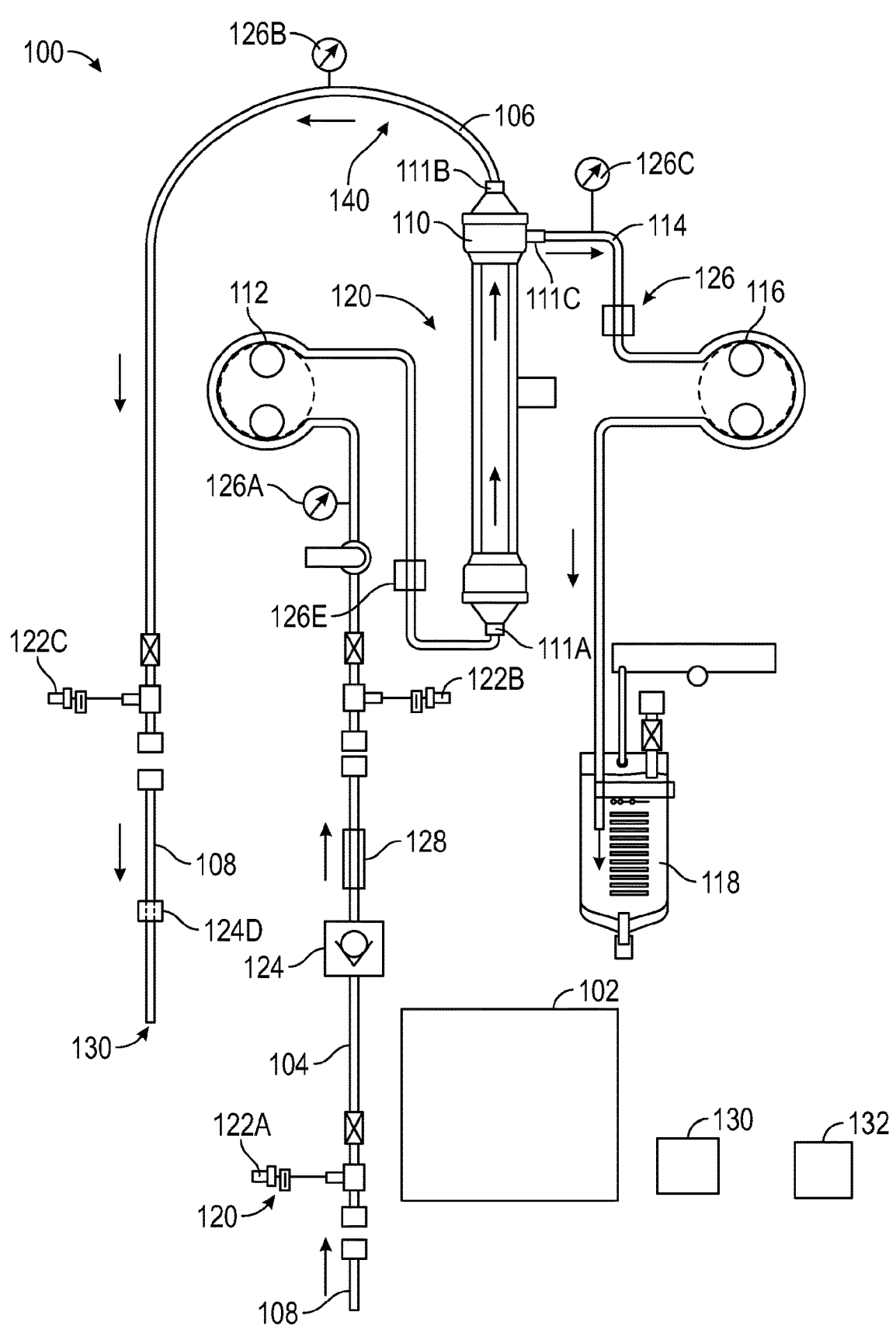
FIG. 1 shows a schematic view of an example of portions of a blood filtration system.

FIG. 1 illustrates a schematic view of an example of portions of a blood filtration system 100, according to an embodiment of the present subject matter. The blood filtration system 100 may reduce one or more plasma constituents (e.g., water, proteins, electrolytes, or the like) in blood of a patient. The blood filtration system 100 may facilitate one or more blood filtration operations, including (but not limited to): extracorporeal ultrafiltration, continuing renal replacement therapy ("CRRT"), slow continuous ultrafiltration ("SCUF"), continuous veno-venous hemofiltration ("CVVH"), continuous veno-venous hemofiltration ("CVVHD"), dialysis, continuous veno-venous hemofiltration including dialysis and filtration ("CVVHDF"), sustained low efficiency dialysis ("SLED"), extracorporeal membrane oxygenation ("ECMO") therapy, modified ultrafiltration, and peripheral plasmapheresis, peripheral hemofiltration.

The blood filtration system 100 may include a controller 102. The controller 102 may include processing circuitry, for instance an integrated circuit or the like. As described herein, the controller 102 may be configured to control one or more components, functions, features, operations, or the like of the blood filtration system 100.

The blood filtration system 100 may include a withdrawal line 104 and may include an infusion line 106. The lines 104, 106 may be configured to couple with a catheter 108, and the lines 104, 106 may transmit blood within the blood filtration system 100. In an example, the catheter 108 may be inserted into a blood stream of the patient, for instance the catheter 108 may be inserted into a basilic vein, cephalic vein, brachial vein, the axillary vein, the subclavian vein, the brachiocephalic vein, or the like. Blood may flow into the catheter 108, into the withdrawal line 104, through other components of the system 100, through the infusion line 106, into the catheter 108, and back into the blood stream of the patient. The line 104 may be separate from the line 106. The lines 104, 106 may be in communication with the catheter 108. For example, the catheter 108 may include one or more lumens, for example a withdrawal lumen in communication with the line 104 and an infusion lumen in communication with the line 106.

The lines 104, 106 may be configured to couple with a filter 110, for instance the lines 104, 106 may include one or more fittings that facilitate coupling the lines 104, 106 with the filter 110. In an example, the withdrawal line 104 may couple with a filter inlet port 111A, and the infusion line 106 may couple with a filter outlet port 111B. The filter 110 may be configured to reduce an amount of one or more plasma constituents (e.g., water, electrolytes, or the like) in blood flowing through the filter 110 and provide a filtrate fluid including the one or more plasma constituents. As described herein, blood may flow through the lines 104, 106 to and from the catheter 108. The lines 104, 106 may be coupled with the filter and blood may flow from the withdrawal line 104, through the filter 110, and into the infusion line 106.

The blood filtration system 100 may include a blood pump 112, and the blood pump 112 may pump (e.g., convey, drive, push, or the like) blood through the blood filtration system 100. In an example, the blood pump 112 may be a peristaltic pump, and the blood pump 112 may engage with the withdrawal line 104 to pump blood through the withdrawal line 104 and into the filter 110. The controller 102 may be configured to operate the blood pump 112 to vary a speed of the blood pump 112 and accordingly vary the flow rate of blood through the blood filtration system 100 (e.g., the withdrawal line 104, the filter 110, the infusion line 106, or the like).

Referring again to FIG. 1, the blood filtration system 100 may include a filtration line 114 and a filtration pump 116. The filtration line 114 may be configured to couple with the filter 110 (e.g., with a fitting), for instance the filtration line 114 may couple with a filtrate fluid port 111C. The filter 110 may be configured to transmit the filtrate fluid (including one or more plasma constituents) extracted by the filter 110 to the filtrate fluid port 111C.

The filtration pump 116 may pump extracted filtrate fluid from the filter 110, and into a filtrate fluid reservoir 118 (e.g., a bag, container, bladder, or the like). In some examples, the filtration pump 116 may be a peristaltic pump that engages with the filtration line 114 to pump the filtrate fluid through the filtrate fluid line 114. The controller 102 may be configured to vary a speed of the filtration pump 116 and accordingly vary the flow rate of filtrate fluid through the blood filtration system 100 (e.g., the filtration line 114).

The system 100 may include a blood circuit 120, and the blood circuit 120 may include one or more components of the system 100, such as may provide a conduit for blood flow. For example, the blood circuit 120 may include (but is not limited to) the withdrawal line 104, the infusion line 106, the catheter 108, the filter 110, the filtration line 114, the filtrate fluid reservoir 118. The blood circuit 120 may include components of the system 100 that are in communication with a biological fluid of the patient.

In some examples, the blood filtration system 100 may include one or more access ports 122, for instance a first access port 122A, a second access port 122B, and a third access port 122C. The access ports 122 may facilitate the extraction of blood from the blood filtration system 100, or injection of substances (e.g., imaging substance, a blood thinner, for instance heparin or the like) into the blood within the blood filtration system 100. In an example, the access ports 122A, 122B may be in communication with the withdrawal line 104, and the access port 122C may be in communication with the infusion line 106.

A valve 124 (e.g., a mechanical check valve, or electronically controlled valve) may be positioned between the access ports 122A, 122B, and the valve 124 may be configured to allow blood to flow unidirectionally within the withdrawal line 104 (e.g., flowing from the catheter 108 to the filter 110). In this example, a substance may be injected into the withdrawal line 104 at the access port 122B, and blood may be withdrawn from the access port 122A. Because the valve 124 facilitates unidirectional flow within the withdrawal line 104, the blood including the substance will not be withdrawn from the access port 122A, for instance because the access port 122A is upstream of the access port 120B). In an example, heparin may be infused into the access port 122B and blood is drawn from the access port 122A to measure blood clotting time parameters of a patient. Because the blood is drawn from the access port 122A, the withdrawn blood does not include heparin, and in an example, a blood clotting time parameter determination is not affected by the heparin injection at the access port 122B. Accordingly, the performance of blood filtration system 100 is thereby improved.

As shown in FIG. 1, the blood filtration system 100 may include one or more sensors 126 (e.g., transducer, accelerometer, or the like), for instance a first sensor 126A, a second sensor 126B, and a third sensor 126C. The first sensor 126A may determine (e.g., measure, obtain, provide, quantify, evaluate, or the like) the pressure within the withdrawal line 104, the second sensor 126B may determine the pressure within the infusion line 106, and the third sensor 126C may determine the pressure within the filtration line 114. The sensors 126 may include a fourth sensor 126D (e.g., a position sensor, or the like) and a fifth sensor 126E (e.g., blood flow rate, or the like), and the sensor 126E may determine the blood flow rate through the system 100 (e.g., a component of the blood circuit 120, for example the withdrawal line 104).

In an example, the blood filtration system includes a cuvette 128 in communication with the blood circuit 120. For example, the cuvette 128 may be in communication with one or more of the withdrawal line 104 or the infusion line 106. In another example, fluid (e.g., blood including one or more plasma constituents, or the like) may be withdrawn from vasculature of a patient and flow through the withdrawal line 104, for instance through a withdrawal lumen of the withdrawal line 104. The cuvette 128 may be in communication with the withdrawal line 104, and fluid flowing through the withdrawal line 104 may flow through the cuvette 128. As described herein, the cuvette may include an optical window that facilitates determination of optical characteristics of the fluid in the cuvette 128. In an example, optical characteristics of the blood include one or more of a wavelength, bandwidth, intensity, frequency, duration, or the like of light transmitted through the fluid and received by an optical sensor. Optical characteristics of the fluid may vary in correspondence with concentrations of substances within the blood, for instance a concentration of red blood cells or a concentration of an imaging substance (e.g., indocyanine green, or the like). In an example, optical characteristics of fluid may vary in correspondence with a concentration of indocyanine green infused in the blood stream of a patient.

Referring to FIG. 1, the blood filtration system 100 may include an optical sensor 130, and the optical sensor 130 may be included in the sensors 126. The optical sensor 130 may determine optical characteristics of fluid in the blood circuit 120 (e.g., fluid in the cuvette 128, or the like). The optical sensor 130 may couple with the blood circuit 120, for instance coupling with cuvette 128. The optical sensor 130 may transmit light through the cuvette 128 to determine the optical characteristics of fluid received in the cuvette 128.

FIG. 1 shows the blood filtration system 100 may include a hematocrit sensor 132, and the hematocrit sensor 132 may be included in the sensors 126. In some examples, the hematocrit sensor 132 is an optical hematocrit sensor. Optionally, the hematocrit sensor 132 may be included in the optical sensor 130. The hematocrit sensor 132 may be coupled with the blood circuit 120, for instance with one or more of the lines 104, 106 or the cuvette 128. The hematocrit sensor 132 may determine a hematocrit value (e.g., level, or the like) of the patient. In an example, the hematocrit sensor 132 may be located between the catheter 108 and the valve 124, for instance to monitor the hematocrit value of the patient prior to injection of a fluid (e.g., heparin or saline) into the blood (e.g., at the access port 122B). Accordingly, the hematocrit value determination may be improved with the system 100.

In an example, the controller 102 may be configured to control the speed of the blood pump 112 and set the flow rate of blood through the filter 110 at a first blood flow rate.

Additionally, the controller 102 may be configured to control the speed of the blood pump 112 and set the flow rate of blood through the filter at a second blood flow rate. The first blood flow rate may be different than the second blood flow rate. The controller 102 may determine the hematocrit at the second blood flow rate. The controller 102 may control the speed of the blood pump 112 and set the flow rate of blood at the first blood flow rate after determining the hematocrit value, for example after determining the hematocrit value at the second blood flow rate.

The controller 102 may control the speed of the blood pump 112 to determine the hematocrit value because the hematocrit value may vary according to the speed of the blood pump 112 (or flow rate of fluid through the blood circuit, such as the cuvette 128) and controlling the speed of the blood pump may improve the accuracy of the hematocrit value determination. For instance, the hematocrit value determination by the hematocrit sensor 132 may be affected by the flow rate of blood through the filter. In this example, the speed of the blood pump 112 can vary, and the determined hematocrit value of the patient may vary according to the speed of the blood pump 112. Accordingly, measuring the hematocrit value with the blood pump 112 at a consistent speed may improve the accuracy of the hematocrit value determination. Accordingly, varying the speed of the blood pump 112 may account for a source of error in determining the hematocrit value and the performance of the blood filtration system 100 is thereby improved.

In another example, the controller 102 records the hematocrit value at a plurality of blood flow rates. For instance, the controller 102 may modulate the blood pump 112 to pump blood through the blood circuit 120 at a first blood flow rate. The controller 102 may determine a first hematocrit value at the first blood flow rate. The controller 102 may modulate the blood pump 112 to pump blood through the blood circuit 120 at a second blood flow rate. The controller 102 may determine a second hematocrit value at the first blood flow rate. In one example, the controller 102 may determine an error value between the first hematocrit value and the second hematocrit value to correct for potential variations in the determined hematocrit value due to changes in blood flow rate. In another example, the controller 102 may generate a look up table based on recorded hematocrit values at the plurality of blood flow rates. For example, the look up table may facilitate correction of potential errors in hematocrit value determinations due to variations in blood flow rate by applying a hematocrit correction to the determined hematocrit values. The hematocrit correction may correspond to the error value between the first hematocrit value and the second hematocrit value. Accordingly, the system 100 may compensate for potential errors in hematocrit value determinations due to variations in blood flow rate through the blood circuit 120.

As described herein, the blood filtration system 100 may determine a hematocrit value of a patient. The hematocrit value of the patient may be expressed as:

$$\text{Hematocrit Value} = \frac{\text{Red Blood Cell Volume}}{\text{Total Blood Volume}}$$

In another example, the total blood volume is equal to the red blood cell volume plus the plasma volume. Accordingly, the hematocrit value of the patient may be expressed as:

$$Hematocrit\ Value = \frac{Red\ Blood\ Cell\ Volume}{Red\ Blood\ Cell\ Volume + Plasma\ Volume}$$

In yet another example, red blood cell volume of a patient may be expressed as:

$$Red\ Blood\ Cell\ Volume = \frac{Plasma\ Volume \times Hematocrit\ Value}{1 - Hematocrit\ Value}$$

Thus, total body red blood cell volume (in contrast to the volume of a single, individual, red blood cell) of a patient may be determined by dividing a first quantity by a second quantity. The first quantity may be equal to the plasma volume multiplied by the hematocrit value of the patient. The second quantity may be equal to 1 minus the hematocrit value of the patient (e.g., a number between 0 and 1). As described herein, the controller 102 may determine one or more of the plasma volume or the hematocrit value of the patient. Accordingly, the controller 102 may determine the red blood cell volume of a patient. In another example, the controller 102 repeatedly determines the red blood cell volume of a patient, for example based on determined optical characteristics of fluid in the blood circuit 120.

In an example, the blood filtration system 100 uses the red blood cell volume to determine a quantity of one or more plasma constituents to extract from the patient. In this example, the red blood cell volume may be input into the blood filtration system 100, for instance at the beginning of therapy. In another example, the controller 102 determines the red blood cell volume, for instance by determining one or more of the plasma volume or the hematocrit value of a patient based on determined optical characteristics of fluid in the blood circuit 120 (e.g., blood in the cuvette 128 shown in FIG. 2, or the like). In some examples, the controller 102 is optionally configured to set an extraction rate of filtrate fluid from the filter 110 using one or more of the determined red blood cell volume, the determined plasma volume, or the determined hematocrit value of the patient.

In another example, the blood filtration system 100 may determine a plasma refill rate of a patient. For instance, the plasma refill rate may include a rate that the plasma volume changes with respect to time, from within the body of the patient (in contrast to a change in plasma volume due to removal of water by the filter). For example, the plasma refill rate may include a rate that plasma water flows into intravascular space from interstitial spaces of the body. The controller 102 may determine the plasma refill rate, for instance by repeatedly determining the plasma volume of a patient and determining a change in the plasma volume of the patient.

The plasma refill rate of a patient may affect the plasma volume determination by the blood filtration system 100. For instance, the plasma refill rate may vary according to one or more factors, including (but not limited to) plasma oncotic pressure, plasma hydrostatic pressure, interstitial osmotic pressure, interstitial hydrostatic pressure, pressure derived from skin turgidity and elasticity, or the like. Accordingly, the plasma refill rate may vary from patient to patient or for one particular patient as therapy proceeds (e.g., the plasma refill rate may be dynamic during therapy for a patient). In an approach, if the extraction rate exceeds the plasma refill rate, the blood filtration system 100 may remove too much plasma fluid from the circulatory system too quickly (e.g., the extraction rate is too high) or in an absolute sense (e.g., total amount of plasma fluid removed during therapy exceeded a specified total). The removal of too much plasma fluid from the circulatory system may lead to hemoconcentration of the blood (excessive rise in hematocrit) with its attendant hyper-viscosity which may increase the likelihood of clotting in the filter. Further, in some approaches, if plasma volume is reduced to a low enough level, the patient may experience reduced blood pressure and tissue perfusion. Accordingly, the blood filtration system helps determine one or more of the plasma refill rate, plasma volume, red blood cell volume, or hematocrit. For instance, the blood filtration system 100 may guide therapy based on the plasma refill rate of the patient, for example by adjusting the extraction rate of filtrate fluid from the filter in proportion to the plasma refill rate.

In an example, the blood filtration system 100 may determine the plasma refill rate and use the plasma refill rate to determine when to stop therapy of the patient, for instance when the patient has reached euvolemia. The controller 102 may determine a quantity of filtrate fluid to extract from the patient. The controller 102 may determine how much plasma remains in the patient at a given point in time, for example to notify a healthcare provider for diagnostic purposes.

In another example, the blood filtration system 100 may guide therapy to provide a patient with an individualized extraction rate and an individualized target plasma volume. For example, the controller 102 may monitor a change in plasma volume of a patient relative to a total starting blood volume of the patient (e.g., a change in plasma volume divided by a starting plasma volume). In an approach, if plasma volume of a patient is above normal, the hematocrit value of the patient may be below a hematocrit threshold. For instance, if the hematocrit value of a patient is below the hematocrit threshold, the controller 102 may determine the patient's blood is hemo-diluted. In another example, as plasma fluid is removed (e.g., with the filter 110), the blood becomes may become hemo-concentrated (e.g., because the filter 110 may refrain from extracting red blood cells). Thus, the controller 102 may monitor changes in the hematocrit value of the patient, for instance to determine relative changes (e.g., on a percentage basis) in plasma volume of the patient. Accordingly, the blood filtration system determines optical characteristics of fluid in the blood circuit, for example to determine plasma volume of a patient (and changes of the plasma volume) during therapy with the blood filtration.

In another example, the blood filtration system 100 determining the red blood cell volume facilitates diagnoses of various types of anemia. For instance, the system 100 may determine the plasma volume and hematocrit value of a patient. Accordingly, the controller 102 may determine the red blood cell volume for the patient. The determined red blood cell volume of a patient may facilitate diagnosis of one or more of dilutional anemia or anemia. For instance, dilutional anemia may include an elevated plasma volume (e.g., in comparison to an expected value given patient demographics, or the like). Anemia may include a diminished red blood cell volume. Accordingly, by determining the plasma volume and red blood cell volume of a patient, the system 100 may help differentiate between dilutional anemia or anemia.

Figure 2:
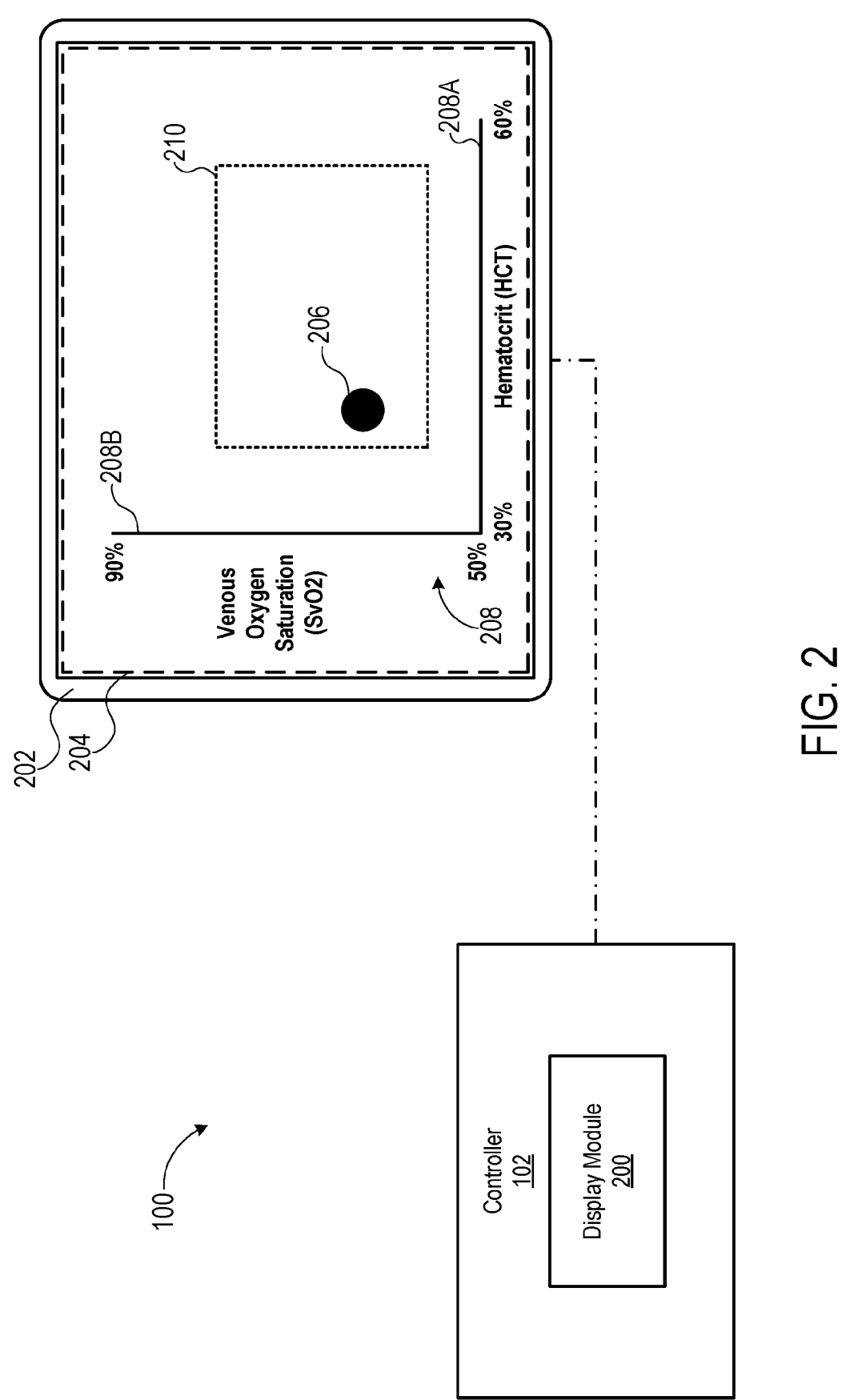
FIG. 2 shows a schematic view of another example of portions of the blood filtration system of FIG. 1.

FIG. 2 illustrates a schematic view of another example of portions of the blood filtration system 100 of FIG. 1. As described herein, the blood filtration system may include one or more of the controller 102 or the sensors 126. The blood filtration system 100 may include a display 202. The controller 102 may cooperate with the display 202 to present content on the display 202.

In an example, the controller 102 may include a display module 200. The display module 200 may generate the content presented on the display 202. For instance, the content generated by the display module 200 may include a diagnostic matrix 204. The diagnostic matrix 204 may include a diagnostic point 206. The diagnostic point 206 may change within the diagnostic matrix 204. For instance, the diagnostic point 206 may change within the diagnostic matrix 204 based on changes in physiological parameters of the patient. In an example, the diagnostic point 206 may change within the diagnostic matrix 204 based on changes in patient physiological parameters including one or more of the hematocrit value, SvO2, relative blood volume, absolute blood volume, plasma volume, oxygen extraction ratio, ejection time, stroke volume, carotid flow time, cardiac output, cardiac power, central venous pressure, mean arterial pressure, systemic vascular resistance, heart rate, respiratory rate, cardiac power, thoracic fluid content, or the like.

As described herein, the diagnostic point 206 may change within the diagnostic matrix 204. For instance, the display module 200 may cooperate with the display 202 to change the diagnostic point 206 within the diagnostic matrix 204. In an example, the display module 200 may move (e.g., translate, reposition, relocate, transpose, or the like) the diagnostic point 206 within the diagnostic matrix 204. For instance, the diagnostic point 206 may move along one or more axis 208. In yet another example, the diagnostic point 206 may move along a first axis 208A and a second axis 208B. For instance, the first axis 208A may be associated with hematocrit values of a patient. The second axis 208B may be associated with venous oxygen saturation ("SvO2") of the patient.

In an example, the diagnostic point 206 may move along the first axis 208A in correspondence with changes in hematocrit values of the patient. For instance, the system 100 may determine the patient has a first hematocrit value at a first time increment. The diagnostic point 206 may be in a first location along the first axis 208A in correspondence with the first hematocrit value at the first time increment. The system 100 may determine the patient has a second hematocrit value at a second time increment. The diagnostic point 206 may be in a second location along the first axis 208A in correspondence with the second hematocrit value at the second time increment. The diagnostic point 206 may move along the second axis 208B in correspondence with changes in the SvO2 of the patient. Accordingly, the diagnostic point 206 may move within the diagnostic matrix 204 in correspondence with changes in physiological parameters of the patient.

In another example, the display module 200 may change a size of the diagnostic point 206 within the diagnostic matrix 204. For instance, the display module 200 may change the size of the diagnostic point 206 in correspondence with changes in physiological parameters of the patient. In an example, the display module 200 may change the size of the diagnostic point 206 in correspondence with changes in relative blood volume of the patient. The diagnostic point 206 may have a first size in correspondence with a first relative blood volume of the patient. The diagnostic point 206 may have a second size in correspondence with a second relative blood volume of the patient. Thus, changes in physiological parameters may change the size of diagnostic point 206.

In yet another example, the display module 200 may change a shape of the diagnostic point 206 within the diagnostic matrix 204. For instance, the display module 200 may change the shape of the diagnostic point 206 in correspondence with changes in physiological parameters of the patient. In an example, the display module 200 may change the shape of the diagnostic point 206 in correspondence with changes in central venous pressure of the patient. The diagnostic point 206 may have a first shape, for instance a circle, in correspondence with a first central venous pressure of the patient. The diagnostic point 206 may have a second shape, for instance a square, in correspondence with a second central venous pressure of the patient. The diagnostic point 206 may have a third shape, including (but not limited to) a rectangle, octagon, polygon, or the like. Thus, changes in physiological parameters may change the shape of diagnostic point 206.

In still yet another example, the display module 200 may change a color of the diagnostic point 206 within the diagnostic matrix. For instance, the display module 200 may change the color of the diagnostic point 206 in correspondence with changes in physiological parameters of the patient. In an example, the display module 200 may change the shape of the diagnostic point 206 in correspondence with changes in plasma volume of the patient. The diagnostic point 206 may have a first color, for instance yellow, in correspondence with a first plasma volume of the patient. The diagnostic point 206 may have a second color, for instance green, in correspondence with a second plasma volume of the patient. The diagnostic point 206 may have a third color, including (but not limited to) red, orange, blue, or the like. Thus, changes in physiological parameters may change the color of diagnostic point 206.

The content presented by the blood filtration system 100 may include a zone of stability 210. For instance, the zone of stability 210 may be presented with the diagnostic matrix 204 on the display 202. The diagnostic point 206 may change with respect to the zone of stability 210. For instance, the diagnostic point 206 may move with respect to the zone of stability 210.

The zone of stability may 210 include a range (e.g., subset, subgroup, division, section, portion, or the like) of values within the values of physiological parameters included in the diagnostic matrix 204. In an example, the first axis 208A may include values of hematocrit between 30 percent and 60 percent. The zone of stability 210 may include a range within the hematocrit values. For instance, the zone of stability 210 may include a range of hematocrit values between 38 percent and 49 percent. In some examples, the zone of stability 210 is user-configurable. For instance, a healthcare provider may set the range of values for the zone of stability 210.

The diagnostic matrix 204 may facilitate maintenance of one or more of cardiovascular stability, hemodynamic stability, or pulmonary stability of a patient. For example, the location of the diagnostic point 206 within the diagnostic matrix 204 may allow a user (e.g., healthcare provider, technician, or the like) to observe the monitored physiological parameters of the patient. The user may observe one or more of the location, trend, movement, size, shape, color, or the like—of the diagnostic point 206 relative to the diagnostic matrix 204. In another example, the user may observe the diagnostic point 206 relative to the zone of stability 210. In an example, the user may adjust operation of the blood filtration system 100 based on observation of the diagnostic point 206 relative to the diagnostic matrix 204 (or the zone of stability 210). For instance, the user may adjust a filtration rate of the blood filtration system 100 based on observation of the diagnostic point 206 relative to the diagnostic matrix 204. The filtration rate may correspond with a rate of removal of filtrate fluid from the blood of the patient. In another example, the user may increase the filtration rate in correspondence with the hematocrit being within the zone of stability 210. In yet another example, the user may decrease the filtration rate in correspondence with the hematocrit outside the zone of stability 210. Accordingly, the blood filtration system 100 may remove fluid from a patient and maintain one or more of cardiovascular stability, hemodynamic stability, or pulmonary stability of the patient.

Figure 3:
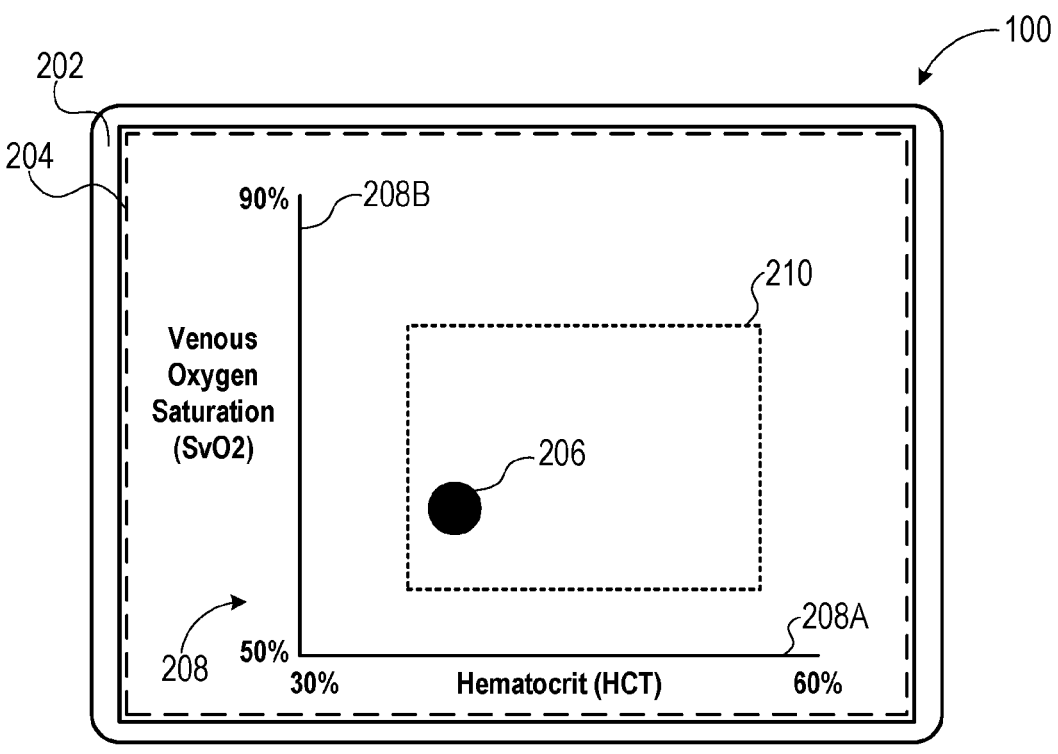
FIG. 3 shows an example of a display presenting content including a diagnostic point along the one or more axis within a diagnostic matrix.
Figure 4:
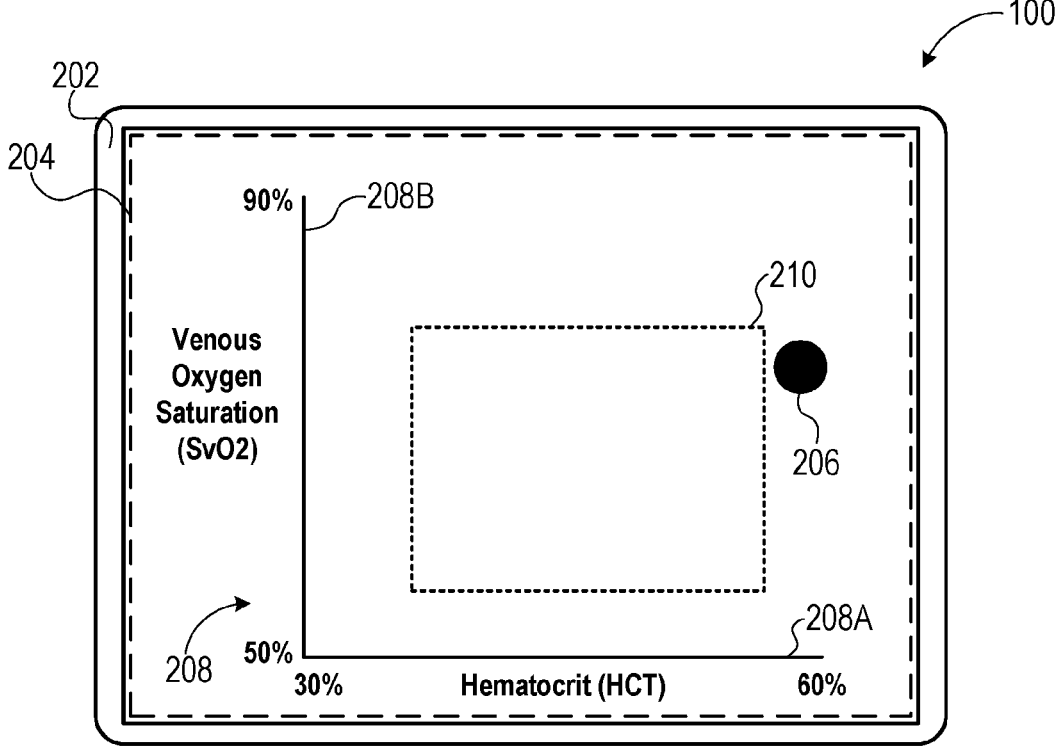
FIG. 4 shows another example of the display presenting the content including the diagnostic point moved along the one or more axis with respect to FIG. 3.

FIGS. 3 and 4 show an example of the display 202 presenting content including the diagnostic point 206 moving along the one or more axis 208 within the diagnostic matrix 204. For instance, the diagnostic point 206 may move in correspondence with changes in physiological parameters monitored by the blood filtration system 100. In an example, FIG. 3 shows the diagnostic point 206 within the zone of stability 210. FIG. 4 shows the diagnostic point 206 outside the zone of stability 210. Accordingly, the diagnostic point 206 may move in correspondence with changes in one or more of the hematocrit value or the SvO2 value of the patient. For instance, the diagnostic point 206 may move from within the zone of stability 210 (shown in FIG. 3) to outside the zone of stability 210 (shown in FIG. 4). In an example, one or more of the hematocrit value and the SvO2 value of the patient may increase in value to move the diagnostic point 206 outside the zone of stability.

Figure 5:
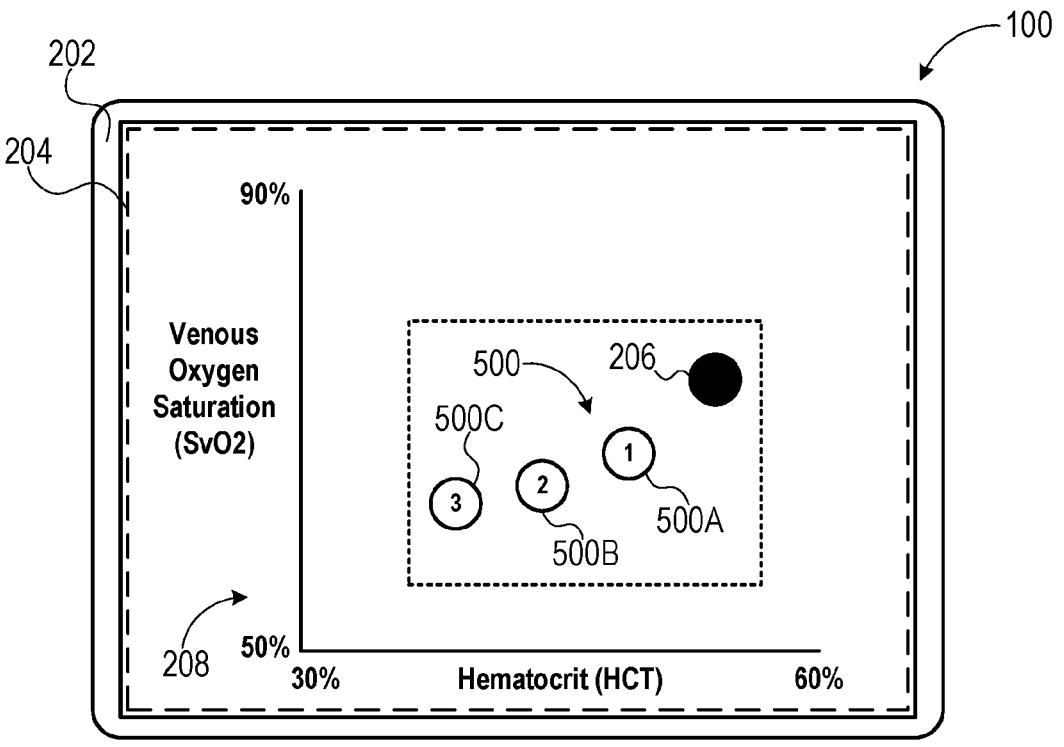
FIG. 5 shows an example of the diagnostic matrix including one or more trend points.
Figure 6:
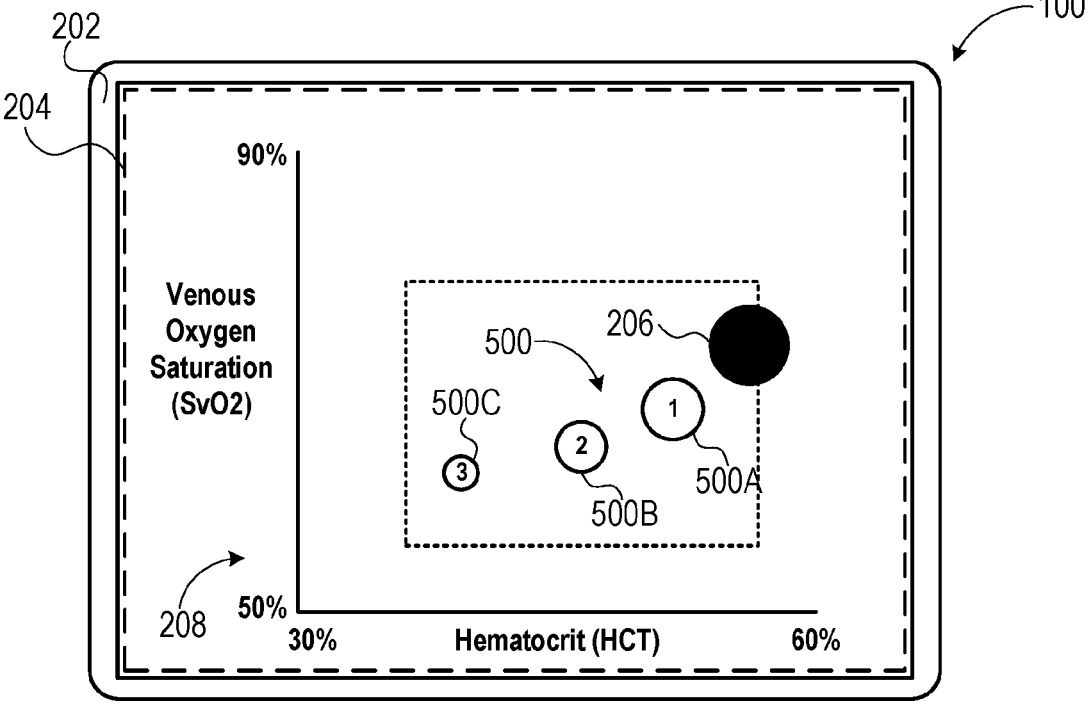
FIG. 6 shows another example of the diagnostic matrix including the one or more trend points.

FIG. 5 and FIG. 6 show the diagnostic matrix 204 may include one or more trend points 500. In an example, the display module 200 (shown in FIG. 2) may cooperate with the display 202 to present the trend points 500. The trend points 500 may facilitate maintenance of one or more of cardiovascular stability, hemodynamic stability, or pulmonary stability of a patient. For instance, the trend points 500 may facilitate monitoring of changes in physiological parameters of the patient. The one or more trend points 500 may correspond with prior (e.g., historical, previous, preceding, or the like) locations of the diagnostic point 206 within the diagnostic matrix 204. In an example, the display module 200 (shown in FIG. 2) may update a location of the diagnostic point 206 at a specified time increment. For instance, the specified time increment may equal 5 seconds, 7 minutes, 15 minutes, 30 minutes, or the like.

FIG. 5 shows the diagnostic point 206 may move along the one or more axis 208. The diagnostic matrix 204 may include a first trend point 500A. The first trend point 500A may correspond with a location of the diagnostic point 206 at a first time increment (e.g., 5 minutes prior to the current location of the diagnostic point 206, or the like). A second trend point 500B may correspond with the location of the diagnostic point 206 at a second time increment (e.g., 10 minutes prior to the first time increment, or the like). A third trend point 500C may correspond with the location of the diagnostic point 206 at a third time increment (e.g., 1 hour prior to second time increment, or the like). Accordingly, the trend points 500 may facilitate observation of a trend of the diagnostic point 206 including the current location of the diagnostic point 206 and the location of the diagnostic point 206 at one or more of the prior time increments.

In another example, the display 202 may present the trend points 500 including indicia 502. The indicia 502 may identify the trend points 500 within the diagnostic matrix 204. For instance, the indicia allow a user to monitor changes in the diagnostic point 206 within the diagnostic matrix 204. In an example, the first trend point 500A may include a "1" identifying the location of the diagnostic point 206 at the first time increment. In another example, the second trend point 500B may include a "2" identifying the location of the diagnostic point 206 at the second time increment. In yet another example, the third trend point 500C may include a "3" identifying the location of the diagnostic point 206 at the third time increment. Accordingly, a user may monitor the trend of the diagnostic point 206 as the diagnostic point 206 changes within the diagnostic matrix 204.

FIG. 6 shows a change in size of the diagnostic point 206. The diagnostic point 206 may change in size in correspondence with changes in physiological parameters of a patient. In an example, the diagnostic point 206 may change in size based on the systemic vascular resistance of the patient. In another example, the trend points 500 may show the diagnostic point 206 having a trend of increasing in size (e.g., diameter, perimeter, area, volume, or the like). For instance, the diagnostic point 206 may be greater in size than the first trend point 500A. Accordingly, the change in size of the diagnostic point 206 (indicated with the trend points 500) may correspond with changes in systemic vascular resistance of the patient. Thus, in an example, the diagnostic point 206 may move within the diagnostic matrix 204 in correspondence with changes in one or more of hematocrit values or SvO2 values of a patient and the diagnostic point 206 may change in size as the diagnostic point 206 moves with respect to the diagnostic matrix 204.

Figure 7:
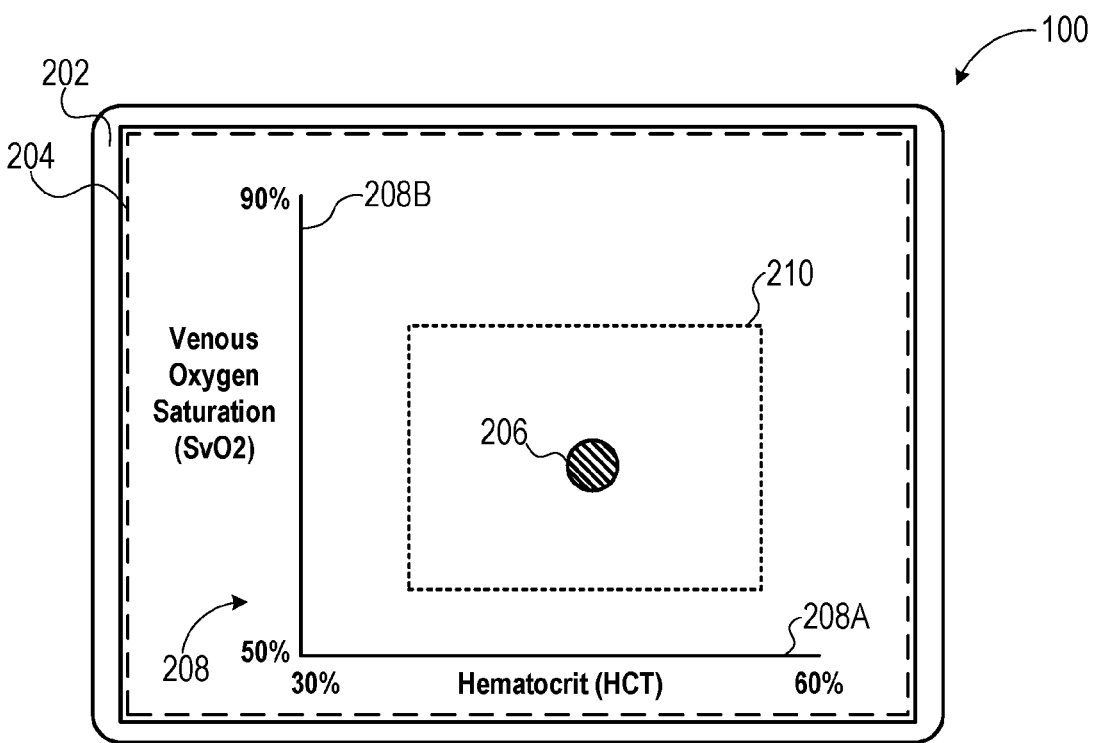
FIG. 7 shows an example of the diagnostic point having a color.
Figure 8:
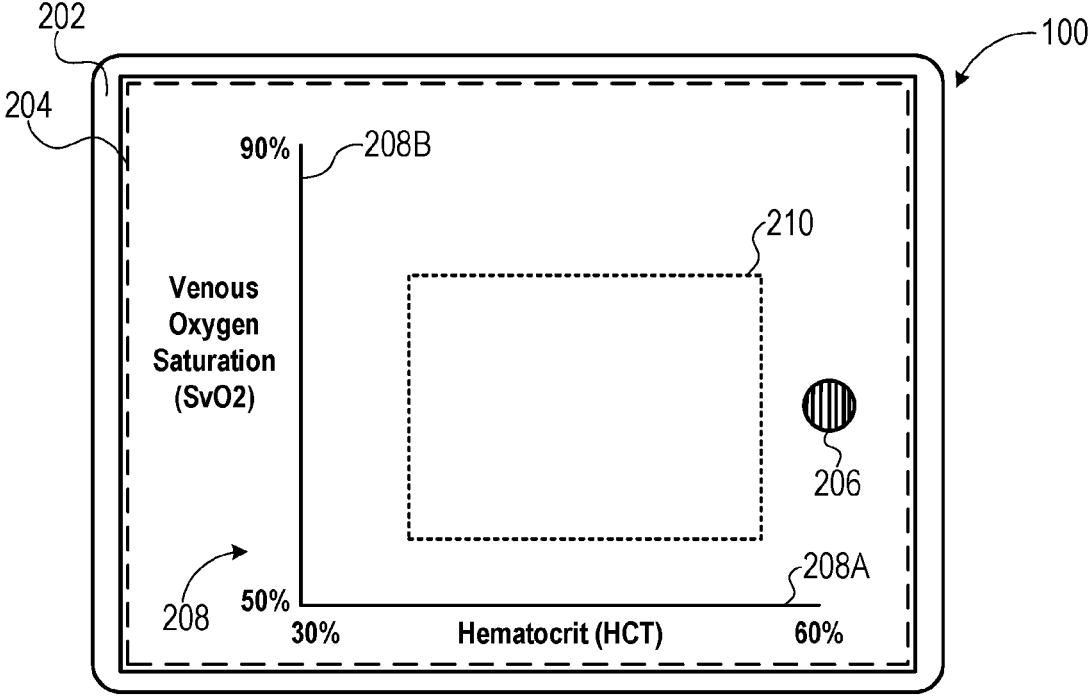
FIG. 8 shows an example of diagnostic point having a different color than the color of the diagnostic point in FIG. 7.

FIG. 7 and FIG. 8 show the diagnostic point 206 may have different colors. For instance, the diagnostic point 206 may change color in correspondence with the physiological parameters. For instance, FIG. 7 shows the diagnostic point 206 may be green in correspondence with the diagnostic point 206 within the zone of stability 210. FIG. 8 shows the diagnostic point 206 may be red in correspondence with the diagnostic point 206 outside the zone of stability 210. The diagnostic point 206 may change color in correspondence with changes in physiological parameters of a patient. Accordingly, in an example, the diagnostic point 206 may change color based on the location of the diagnostic point 206 within the diagnostic matrix 204.

Figure 9:
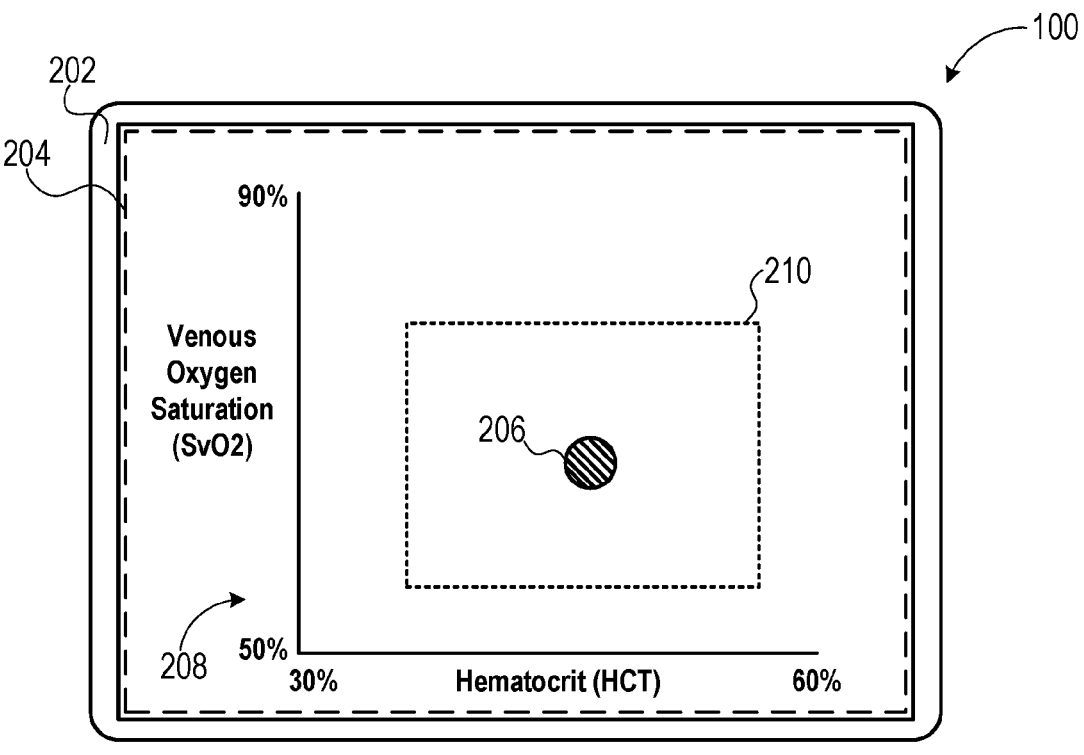
FIG. 9 shows an example of the diagnostic point within the diagnostic matrix.
Figure 10:
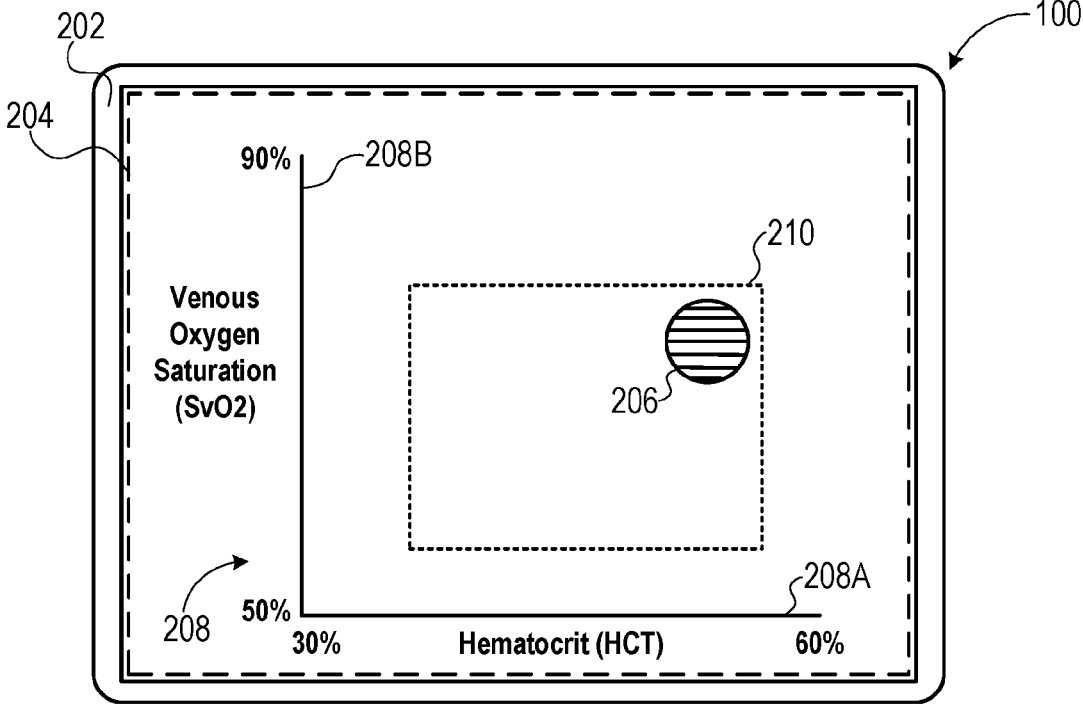
FIG. 10 shows another example of the diagnostic point within the diagnostic matrix.

FIG. 9 and FIG. 10 show the diagnostic point 206 may change within the diagnostic matrix 204 based on changes in physiological parameters of the patient. In an example, the diagnostic point 206 may move within the diagnostic matrix 204. For instance, FIG. 9 shows the diagnostic point 206 in a first location within the diagnostic matrix 204 (e.g., corresponding to a first set of values for HCT and SvO2, or the like). For instance, FIG. 9 shows the diagnostic point 206 may be proximate a center of the zone of stability 210. FIG. 10 shows the diagnostic point 206 in a second location (e.g., corresponding to a second set of values for HCT and SvO2, or the like). For example, FIG. 10 shows the diagnostic point 206 may be proximate an edge of the zone of stability 210.

The diagnostic point 206 in FIG. 9 may have a first size. The diagnostic point 206 in FIG. 10 may have a second size. For instance, the diagnostic point 206 in FIG. 10 may be larger in size than the diagnostic point 206 in FIG. 9. In an example, the diagnostic point 206 may change in size based on changes in relative blood volume (or other physiological parameters of the patient). In yet another example, FIG. 9 shows the diagnostic point may be green in color. FIG. 10 shows the diagnostic point 206 may be blue in color. The diagnostic point 206 may change color based on changes in respiratory rate (or other physiological parameters of the patient). Accordingly, changes in physiological parameters of a patient may correspondingly change the diagnostic point 206 within the diagnostic matrix 204.

The relative blood volume (RBV) may correspond with a percentage change in blood volume. In an example, relative blood volume includes a hematocrit value at a first time interval (HCT1). In another example, the relative blood volume may include a hematocrit value at a second time interval (HCT2)

$$RBV = \left(\frac{HCT1}{HCT2} - 1\right) * 100$$

Figure 11:
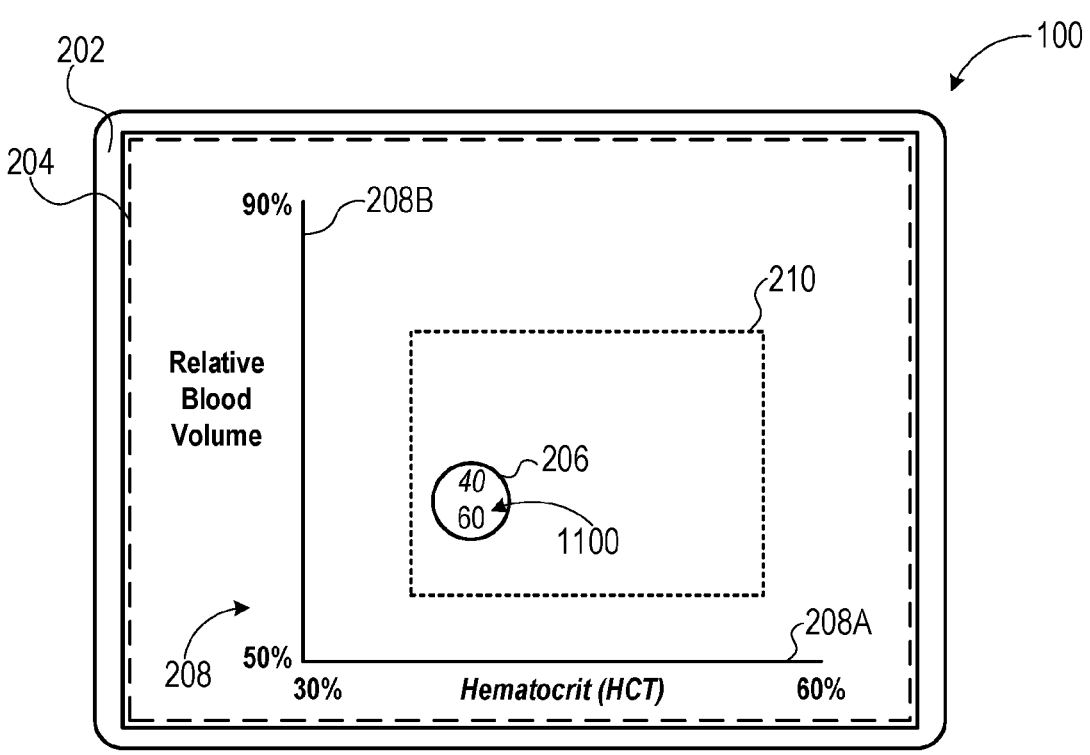
FIG. 11 shows an example of the diagnostic matrix presenting content corresponding to physiological parameters of a patient.
Figure 12:
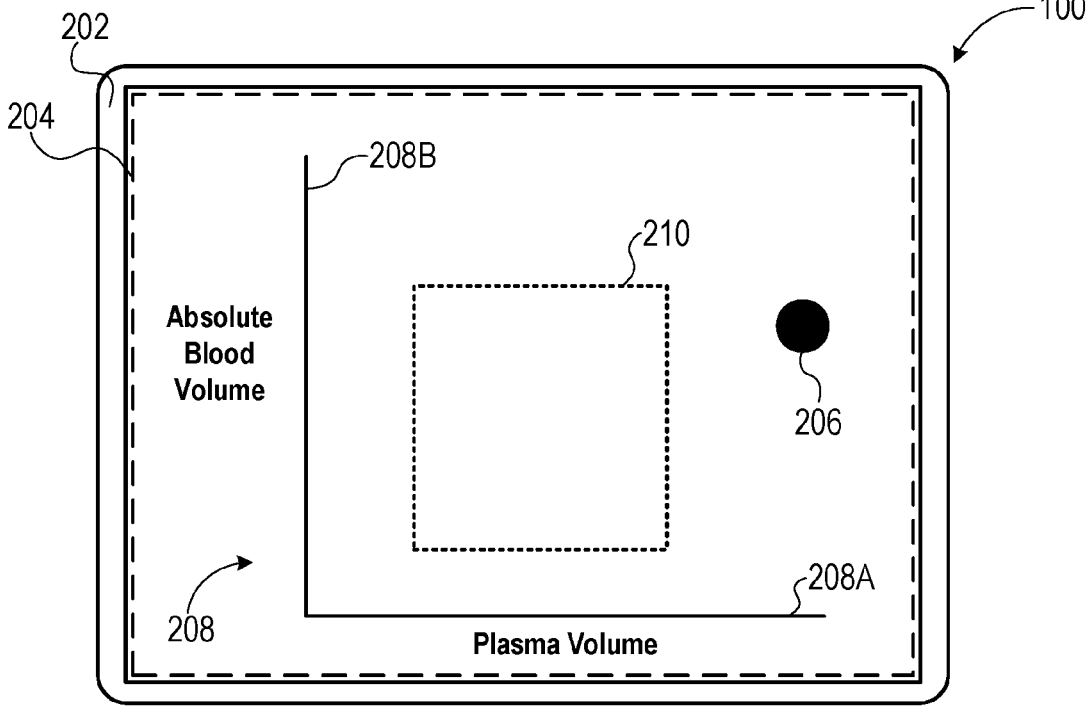
FIG. 12 shows another example of the diagnostic matrix presenting content corresponding to physiological parameters of a patient.

FIG. 11 and FIG. 12 show the diagnostic matrix 204 presenting content corresponding to physiological parameters of a patient. In an example, the diagnostic matrix 204 may be user-configurable to change the physiological parameters presented in the diagnostic matrix 204. For instance, the diagnostic matrix 204 may include hematocrit values of the patient along the first axis 208A. The diagnostic matrix 204 may include relative blood volume values of the patient along the second axis 208B. In another example, FIG. 12 shows the first axis 208A may be associated with plasma volume values of a patient. In yet another example, FIG. 12 shows the second axis 208B may be associated with the absolute blood volume of the patient. The axis 208 may be associated with other physiological parameters of the patient. For instance, the axis 208 may be associated with the physiological parameters of the patient including (but not limited to) hematocrit value, SvO2, relative blood volume, absolute blood volume, plasma volume, oxygen extraction ratio, ejection time, stroke volume, carotid flow time, cardiac output, cardiac power, central venous pressure, mean arterial pressure, systemic vascular resistance, heart rate, respiratory rate, cardiac power, thoracic fluid content, or the like. Accordingly, display 202 may present the diagnostic matrix 204 including values for one or more of the physiological parameters of a patient.

The diagnostic point 206 may include indicia 1100. For instance, the indicia 1100 may correspond with values of the physiological parameters. In an example, the indicia 1100 may indicate the values associated with the location of the diagnostic point 206 within the diagnostic matrix 204. Thus, the indicia 1100 may provide a user with a reference for the monitored value of physiological parameters included in the diagnostic matrix 204.

Figure 13:
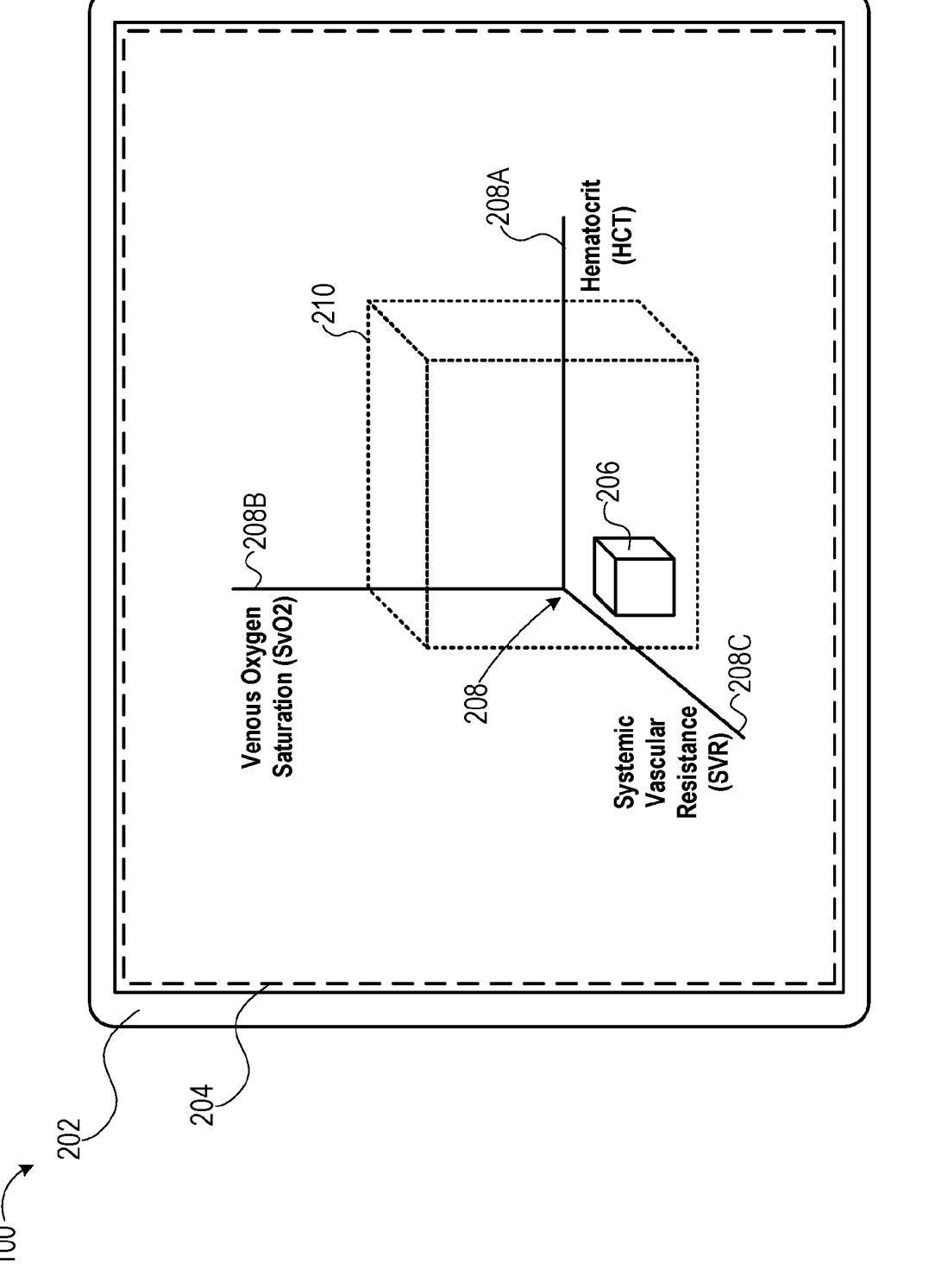
FIG. 13 shows an example of the diagnostic matrix having a third axis.
Figure 14:
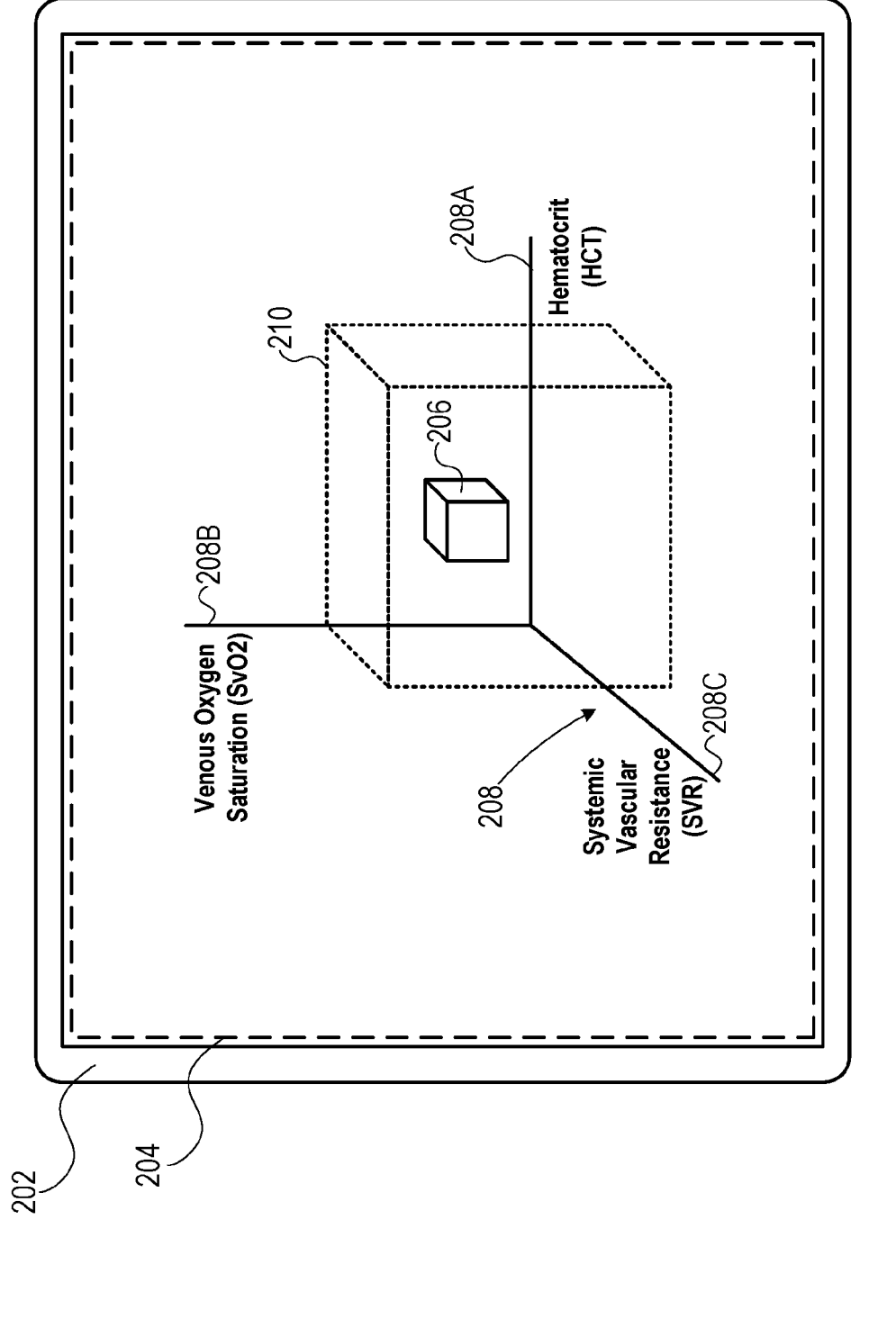
FIG. 14 shows another example of the diagnostic matrix having a third axis.

FIG. 13 and FIG. 14 show the diagnostic matrix 204 may have a third axis 208C. Accordingly, the diagnostic matrix 204 may be multi-dimensional. As described herein, the one or more axis 208 may be associated with physiological parameters of a patient. In an example, the first axis 208A may be associated with a hematocrit value of a patient. The second axis 208B may be associated with an SvO2 value of the patient. The third axis 208C may be associated with a systemic vascular resistance value of the patient.

The diagnostic point 206 may change within the diagnostic matrix 204. In an example, the diagnostic point 206 may move along the one or more axis 208 of the diagnostic matrix 204. For example, the diagnostic point 206 may move within the diagnostic matrix 204 in correspondence with changes in one or more of the hematocrit value, SvO2 value, or SVR value of the patient. FIG. 13 shows the diagnostic point 206 may be in a first location within the diagnostic matrix 204. FIG. 14 shows the diagnostic point may be in a second location within the diagnostic matrix 204. Accordingly, the diagnostic matrix 204 may include content associated with one or more of the physiological parameters of a patient. A user may monitor the physiological parameters of the patient using the diagnostic matrix 204. For instance, the user may monitor changes in the diagnostic point 206 within the diagnostic matrix 204 to correspondingly monitor the physiological parameters of the patient. Thus, the user may maintain one or more of cardiovascular stability, hemodynamic stability, or pulmonary stability of the patient using the blood filtration system 100.

Figure 15:
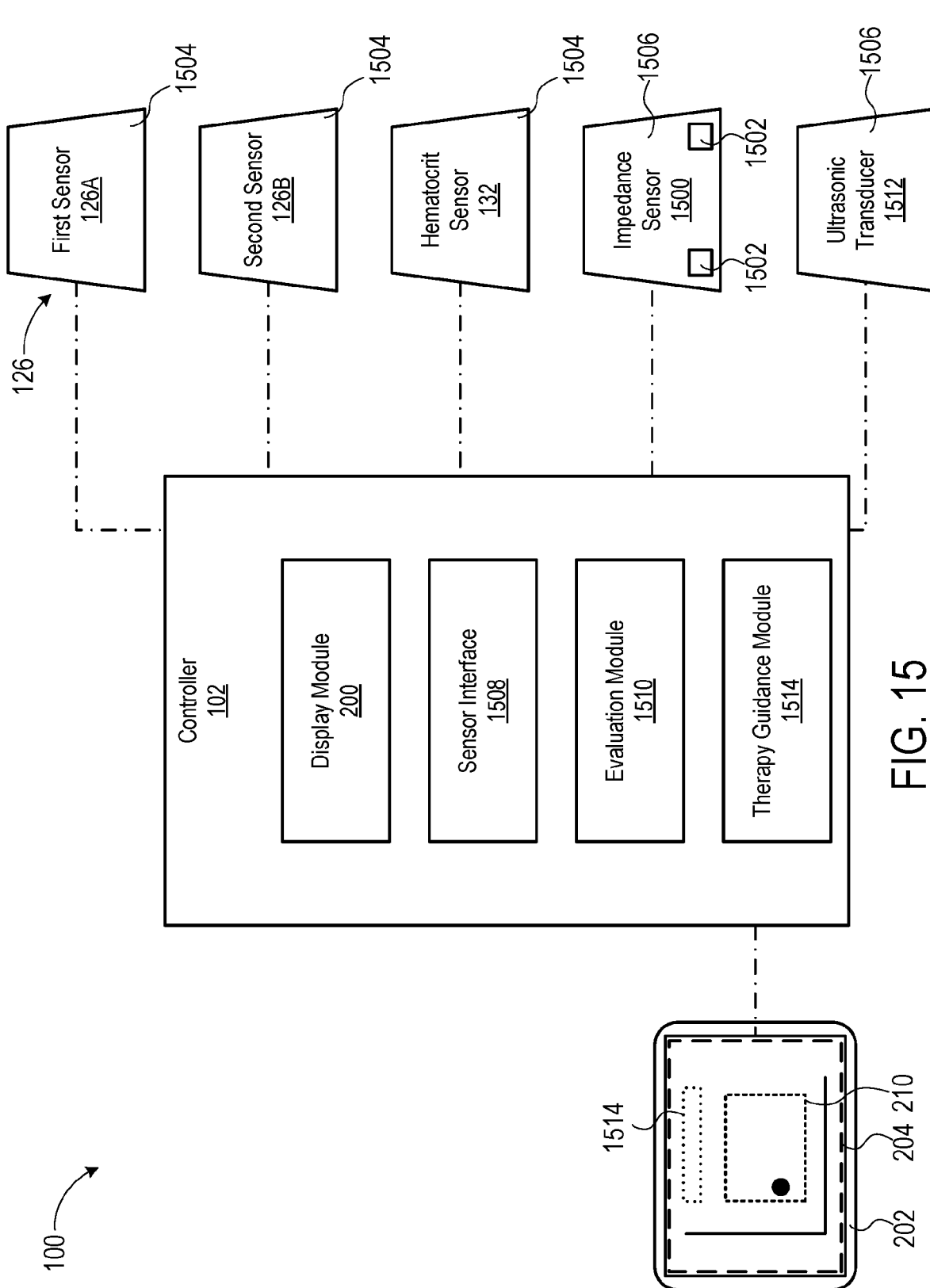
FIG. 15 shows a schematic view of yet another example of portions of the blood filtration system of FIG. 1.

FIG. 15 shows a schematic view of yet another example of portions of the blood filtration system 100 of FIG. 1. In an example, the blood filtration system may include one or more of the controller 102, the sensors 126, or the display 202. For instance, the controller 102 may include the display module 200. The display module 200 may cooperate with the display 202 to present the diagnostic matrix 204.

In another example, the blood filtration system 100 may use the sensors 126 to determine one or more physiological parameters of a patient. For instance, the sensors 126 may include one or more of the first sensor 126A, the second sensor 126B, the hematocrit sensor 132, or an impedance sensor 1500. The first sensor 126A may determine (e.g., measure, obtain, provide, quantify, evaluate, or the like) the pressure within portions of the blood circuit 120 (shown in FIG. 1). The first sensor 126A may determine the pressure in one or more of the withdrawal line 104 or the infusion line 106. In another example, the second sensor 126B may determine the pressure within the infusion line 106. As described herein, and referring to FIG. 1, the withdrawal line 104 or the infusion line 106 may communicate with vasculature of a patient. In an example, the catheter 108 may be inserted into a blood stream of the patient, for instance the catheter 108 may be inserted into a basilic vein, cephalic vein, brachial vein, the axillary vein, the subclavian vein, the brachiocephalic vein, or the like. Blood may flow into the catheter 108, into the withdrawal line 104, through other components of the system 100, through the infusion line 106, into the catheter 108, and back into the blood stream of the patient. Accordingly, one or more of the first sensor 126A or the second sensor 126B may determine pressure in the vasculature of the patient. For instance, the sensors 126 may determine central venous pressure, mean arterial pressure, jugular venous pulse, or the like.

Referring to FIG. 15, the sensors 126 may include the hematocrit sensor 132. The hematocrit sensor 132 may be coupled with the blood circuit 120, for instance with one or more of the lines 104, 106 or the cuvette 128. The hematocrit sensor 132 may determine a hematocrit value (e.g., level, or the like) of the patient.

In yet another example, the sensors 126 may include the impedance sensor 1500. For instance, the blood filtration system 100 may determine physiological parameters of a using an impedance sensor 1500. The impedance sensor 1500 may communicate with a body of the patient. For instance, the impedance sensor 1500 may communicate with the body of the patient to determine an impedance of the body of the patient.

The blood filtration system 100 may use the impedance of the body to determine the physiological parameters of the body. For instance, the physiological parameters of the patient may change in correspondence with changes in the impedance of the body of the patient. In another example, the impedance sensor 1500 may communicate with a thorax of the patient. Accordingly, the impedance sensor 1500 may determine an impedance of the thorax of the patient. In yet another example, the blood filtration system 100 may use one or more of impedance cardiography, impedance pneumology, or the like to determine the physiological parameters of the patient. For instance, the impedance sensor 1500 may use one or more electrodes 1502 to determine pulmonary fluid content of the patient. In yet another example, the impedance sensor 1500 uses the one or more electrodes 1502 to determine cardiac functions of the patient, including (but not limited to) cardiac output, cardiac power, ejection time, stroke volume, or the like. Thus, the blood filtration system 100 may use the impedance sensor 1500 to determine the impedance of the body (and physiological parameters associated with the impedance of the body).

The sensors 126 may be invasive or non-invasive. For example, one or more of the first sensor 126A or the second sensor 126B may communicate with vasculature of the patient. Accordingly, the blood filtration system 100 may include one or more invasive sensors 1504 that communicate with bodily fluids of a patient. For instance, the first sensor 126A may determine pressure in the vasculature (e.g., central venous pressure, or the like) of the patient. In another example, the second sensor 126B may determine pressure in the vasculature (e.g., mean arterial pressure, or the like) of the patient.

In yet another example, the one or more invasive sensors 1504 may include the hematocrit sensor 132. For instance, the hematocrit sensor 132 may determine optical characteristics of blood of a patient. The optical characteristics of the blood may correspond with the hematocrit value of the patient. Accordingly, the invasive sensors 1504 may communicate with internal portions of the body of the patient (or internal fluids of the patient), for instance by puncturing the skin of the patient (e.g., with the catheter 108, shown in FIG. 1, inserted into a vein, or the like).

The blood filtration system may include one or more non-invasive sensors 1506. The non-invasive sensors 1506 may include the impedance sensor 1500. In an example, the one or more electrodes 1502 may be secured to a body of a patient. In another example, the electrodes 1502 may engage skin of the patient. Thus, the non-invasive sensor 1506 may communicate with the body of the patient without puncturing skin of the patient (e.g., by transmitting a signal through the skin, or the like). For instance, the non-invasive sensor 1506 may determine an impedance (or change in impedance) of the body of the patient.

In still yet another example, the blood filtration system 100 may determine at least the systemic vascular resistance of a patient using both the invasive sensors 1504 and the non-invasive sensors 1506. For instance, the systemic vascular resistance may be based on one or more of mean arterial pressure, central venous pressure, or cardiac output. The blood filtration system 100 may monitor one or more of the central venous pressure or the mean arterial pressure using one or more of the sensors 126 (e.g., the first sensor 126A, second sensor 126B, or the like) in communication with vasculature of the patient. Monitoring the central venous pressure or the mean arterial pressure may enhance the accuracy of determining the systemic vascular resistance.

In some approaches, the central venous pressure may be estimated in correspondence with systemic vascular resistance determinations. In another approach, the central venous pressure may be determined by a user. For instance, the user may input the central venous pressure into the blood filtration system. In this approach, the system may determine the systemic vascular resistance using the user-determined central venous pressure.

The blood filtration system 100 may repeatedly determine the central venous pressure of the patient using the sensors

126 (e.g., the first sensor 126A, or the like). The blood filtration system 100 may determine the systemic vascular resistance based on the repeatedly determined central venous pressure. In another example, the blood filtration system 100 may use the repeatedly determined central venous pressure of the patient to determine the systemic vascular resistance of the patient.

The blood filtration system 100 may repeatedly determine the mean arterial pressure of the patient using the sensors 126 (e.g., the second sensor 126B, or the like). The blood filtration system 100 may determine the systemic vascular resistance based on the repeatedly determined central venous pressure. In another example, the blood filtration system 100 may use the repeatedly determined central venous pressure of the patient to determine the systemic vascular resistance of the patient.

In yet another example, the blood filtration system 100 may monitor the cardiac output of the patient using the impedance sensor 1500. Accordingly, accuracy of the systemic vascular resistance determination is enhanced, for instance because the blood filtration system 100 monitors the physiological parameters using the invasive sensors 1504 (e.g., one or more of the first sensor 126A, second sensor 126B, or the hematocrit sensor 132, or the like) and the non-invasive sensors 1506 (e.g., the impedance sensor 1500, or the like). In an example, the blood filtration system 100 repeatedly determines the systemic vascular resistance based on physiological parameters received from the invasive sensors 1500 and the non-invasive sensors. For instance, blood filtration system may monitor changes in the central venous pressure to enhance the accuracy the systemic vascular resistance determined with the blood filtration system. In another example, the blood filtration system 100 may monitor changes in the cardiac output to enhance the accuracy of the systemic vascular resistance determined with the blood filtration system 100 Thus, the blood filtration system 100 may determine physiological parameters with enhanced accuracy, for instance because the blood filtration system communicates with the invasive sensors 1504 (e.g., a pressure sensor, or the like) and the non-invasive sensors 1506 (e.g., the impedance sensor 1500, or the like). Accordingly, the diagnostic matrix 204 may present physiological parameters having enhanced accuracy.

Referring to FIG. 15, the controller 102 may communicate with the sensors 126. For example, the controller 102 may include a sensor interface 1508. The sensor interface 1508 may receive physiological parameters determined by the sensors 126. Accordingly, the sensors 126 may determine the physiological parameters. The sensors may communicate the physiological parameters to the controller 102 using the sensor interface 1508.

The controller 102 may determine one or more physiological parameters of a patient using the sensors 126. For example, the controller 102 may communicate with the hematocrit sensor 132. The controller 102 may include an evaluation module 1510. In an example, the evaluation module 1510 may determine a hematocrit value of a patient based on optical characteristics (or changes in optical characteristics) determined by the hematocrit sensor 132. In another example, the evaluation module 1510 uses the impedance sensor 1500 to determine one or more of cardiac output, cardiac power, ejection time, stroke volume, cardiac power or the like. For instance, the evaluation module 1510 may determine stroke volume of a patient based on impedance (or changes in impedance) of the body of the patient.

In an example, the following equations and derivations demonstrate the correspondence between changes in electrical impedance in the thorax or body generally to volumetric changes (e.g., cardiac output, stroke volume, or the like). For instance, Equation 1 includes total body impedance (Zt), impedance of the thorax (Zth), and impedance of the blood of the patient (Zb):

$$Zt = \frac{Zb * Zth}{Zb + Zth} \qquad \text{Equation 1}$$

Equation 2 defines the impedance of the body other than the thorax (Zb). Equation 2 includes the resistivity of blood (ρb), length of the body (l), and area of the body other than thorax (Ab). In some examples, the blood filtration system 100 may monitor changes in the resistivity of blood (ρb) based on changes in the total body impedance (Zb).

$$Zb = \frac{\rho b * l}{Ab} \qquad \text{Equation 2}$$

Equation 3 defines the volume of the body of the patient (Vb).

$$Vb = Ab * l \qquad \text{Equation 3:}$$

Equation 4 is the partial derivative of Zt with respect to Zb. Algebraically manipulating Equation 4 yields Equation 5.

$$\frac{\partial Zt}{\partial Zb} = \frac{Zt(Zth + Zb) - Zh * th * Zb}{(Zth + Zb)^2} \qquad \text{Equation 4}$$

$$\frac{\partial Zt}{\partial Zb} = \frac{(Zth)^2}{(Zth + Zb)^2} = \frac{(Zt)^2}{(Zb)^2} \qquad \text{Equation 5}$$

Equation 6 includes algebraically manipulating Equation 2 and substituting the algebraically manipulated Equation 2 into Equation 3.

$$Vb = \frac{\rho b * l^2}{Zb} \qquad \text{Equation 6}$$

Equation 7 is the partial derivative of Vb with respect to Zb.

$$\frac{\partial Vb}{\partial Zb} = -\frac{\rho b * l^2}{(Zb)^2} \qquad \text{Equation 7}$$

Equation 8 multiplies Equation 7 and Equation 5. Algebraically manipulating Equation 8 yields Equation 9. Additionally, algebraically manipulating Equation 9 yields Equation 10.

$$\left(\frac{\partial Zt}{\partial Zb}\right) * \left(\frac{\partial Zb}{\partial Vb}\right) = -\frac{(Zt)^2}{(Zb)^2} \qquad \text{Equation 8}$$

$$\frac{\partial Zt}{\partial Vb} = -\frac{(Zt)^2}{\rho b * l^2} \qquad \text{Equation 9}$$

$$\frac{\partial Vb}{\partial Zt} = -\frac{\rho b * l^2}{(Zt)^2} \qquad \text{Equation 10}$$

Equation 11 includes algebraically manipulating Equation 10, and taking the partial derivative of Vb with respect to time (t).

$$\frac{\partial Vb}{\partial t} = -\left(\frac{\rho b * l^2}{(Zt)^2}\right) * \left(\frac{\partial Zt}{\partial t}\right) \qquad \text{Equation 11}$$

Accordingly, Equation 11 describes a change in volume with respect to time. Applying Equation 11 to an aorta of a patient yields Equation 12. Equation 12 describes the volume of blood pumped into the aorta of the patient with each heartbeat of the patient. In another example, Equation 12 describes the stroke volume of the patient.

$$\text{Stroke Volume} = -\left(\frac{\rho b * l^2}{(Zt)^2}\right) * \left(\frac{dZt}{dt}\right) * t_{ejection} \qquad \text{Equation 12}$$

Equation 12 includes a duration of ventricular ejection ($t_{ejection}$). In another example, $t_{ejection}$ corresponds with the left ventricular ejection time (LVET). Accordingly, Equation 13 substitutes LVET for $t_{ejection}$ in Equation 12.

$$SV = -\left(\frac{\rho b * l^2}{(Z_t)^2}\right) * \left(\frac{dZ_t}{dt}\right) * LVET \qquad \text{Equation 13}$$

In an example, Equation 13 shows the physiological parameters that affect stroke volume (SV) using the impedance sensor 1500. Referring to FIG. 15, the LVET may have a direct proportional effect on the stroke volume determined by the evaluation module 1510. Accordingly, the present inventors have recognized that a problem to be solved may include increasing accuracy of the evaluation module 1510 determining the stroke volume. The present subject matter can help provide a solution to this problem, such as by enhancing accuracy of determining physiological parameters that affect the stroke volume. In an example, one or more of the baseline total body impedance (Zt) or the blood resistivity (ρb) change as filtrate fluid is removed with the system 100. The impedance sensor 1500 may determine one or more of the baseline total body impedance (Zt) or the blood resistivity (ρb).

In an example, as filtrate fluid is removed with the system 100, the baseline total body impedance (Zt) may decrease. In another example, the blood resistivity (ρb) may decrease as filtrate fluid is removed with the system 100. Accordingly, the blood filtration system 100 may monitor physiological parameters the physiological parameters that affect the stroke volume. For instance, the evaluation module 1510 may determine the stroke volume of a patient based on one or more of the baseline total body impedance (Zt) or the blood resistivity (ρb). In another example, the evaluation module 1510 may determine the stroke volume of a patient based on changes in one or more of the baseline total body impedance (Zt) or the blood resistivity (ρb). Thus, the blood filtration system 100 may determine the stroke volume of the patient with enhanced accuracy.

In another example, Equation 14 defines the cardiac output of the patient. The cardiac output of the patient is equal to the stroke volume of the patient multiplied by the heart rate of the patient.

$$CO = SV * HR \qquad \text{Equation 14:}$$

Referring to FIG. 15, the blood filtration system 100 may use the impedance sensor 1500 to determine the heart rate of the patient. Accordingly, the controller 102 may cooperate with the impedance sensor 1500 to determine the cardiac output of the patient. For instance, the sensor interface 1508 may monitor one or more of the baseline total body impedance (Zt), the blood resistivity (ρb), or the heart rate of the patient using the impedance sensor 1500. The evaluation module 1510 may use monitored physiological parameters to determine the cardiac output of the patient. The evaluation module 1510 may enhance the accuracy of the cardiac output determination by monitoring one or more of the baseline total body impedance (Zt), the blood resistivity (ρb), or the heart rate of the patient. For instance, one or more of the baseline total body impedance (Zt), the blood resistivity (ρb), or the heart rate of the patient may change as filtrate fluid is removed from blood of the patient. Monitoring of one or more of the baseline total body impedance (Zt), the blood resistivity (ρb), or the heart rate of the patient may allow the blood filtration system 100 may compensate for changes in the cardiac output based on changes in the total body impedance (Zt), the blood resistivity (ρb), or the heart rate of the patient. Thus, the blood filtration system 100 may use the impedance sensor 1500 to enhance the accuracy of physiological parameters determined with the controller 102.

The blood filtration system 100 may determine the ejection time (or LVET) using the impedance sensor 1500. In another example, the blood filtration system 100 may include an ultrasonic transducer 1512. The non-invasive sensors 1506 may include the ultrasonic transducer 1512. The system 100 may use the ultrasonic transducer 1512 to determine the ejection time of a patient. For instance, the system 100 may determine the ejection time with enhanced accuracy by using the ultrasonic transducer 1512. For instance, determining the ejection time with the ultrasonic transducer 1512 may be more accurate than determining the ejection time with the impedance sensor 1500. Accordingly, the controller 102 may communicate with the ultrasonic transducer to monitor the ejection time of a patient. The controller 102 may use the ejection time of the patient in correspondence with other physiological parameters, for instance cardiac output. Thus, the ultrasonic transducer 1512 may enhance the accuracy of determining physiological parameters with the blood filtration system 100.

In an example, the blood filtration system 100 may monitor one or more heart sounds of a patient using the ultrasound transducer 1512. The ultrasonic transducer 1512 may determine the velocity of blood flow in vasculature of a patient, including (but not limited to) a carotid artery of the patient. The sensor interface 1508 may communicate with the ultrasonic transducer 1512 to monitor the velocity of blood flow in the carotid artery.

In another example, the evaluation module 1510 may determine the ejection time of the patient using the monitored heart sounds of the patient. For instance, evaluation module 1510 may determine the ejection time based on the monitored velocity of blood flow in the carotid artery. In an example, the evaluation module 1510 may identify a first heart sound (S1) of the patient using the ultrasonic transducer 1512. The first heart sound (S1) may correspond with closure of mitral and tricuspid valves (e.g., associated with the start of systole, or the like). The evaluation module 1510 may identify a second heart sound (S2) of the patient using the ultrasonic transducer 1512. The second heart sound (S2) may correspond with closure of the aortic and pulmonic valves (e.g., associated with the end of systole, or the like).

The ejection time may correspond with the difference between the first heart sound (S1) and the second heart sound (S2). In an example, the evaluation module 1510 may identify the first heart sound (S1) and the second heart sound (S2) using the monitored velocity of blood flow in the carotid artery. Accordingly, the evaluation module 1510 may determine the ejection time based on the difference in time between the first heart sound (S1) and the second heart sound (S2).

Figure 16:
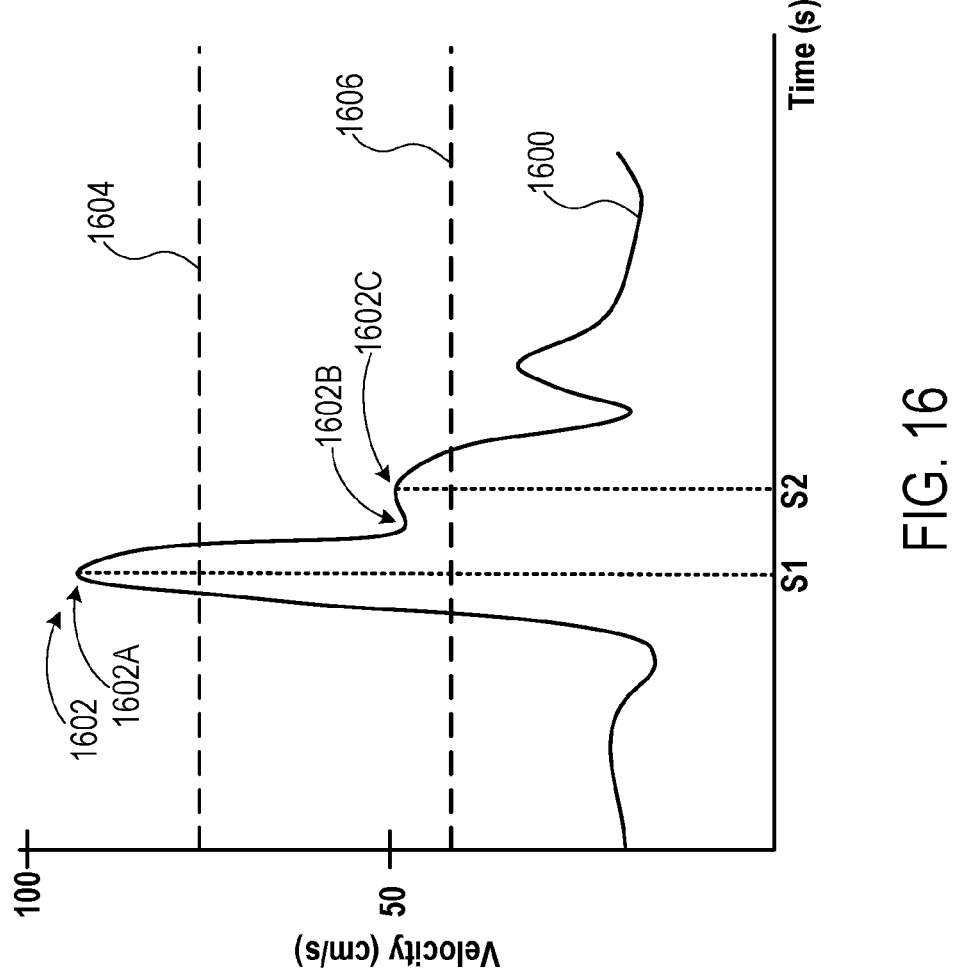
FIG. 16 shows an example of a velocity corresponding to the monitored velocity of blood flow in vasculature.

FIG. 16 shows an example of a velocity waveform 1600 (e.g., signal, or the like) corresponding to the monitored velocity of blood flow in vasculature, for instance velocity of blood flow in a carotid artery of a patient. The ultrasonic transducer 1512 may determine the velocity of blood flow in the carotid artery. The evaluation module 1510 may identify heart sounds using the velocity waveform 1600. For instance, the evaluation module 1510 may identify one or more of the first heart sound (S1) or the second heart sound (S2) using the velocity waveform 1600. In an example, the evaluation module 1510 may identify one or more inflection points 1602 in the velocity waveform 1600 corresponding to heart sounds of the patient. In an example, the inflection points 1602 may include one or more of a change in magnitude of a derivative of the velocity waveform 1600, such as an increase in the rate that the slope is decreasing; a change in sign of the slope of the velocity waveform 1600; a change in sign of the derivative of velocity waveform 1600; peaks and valleys; or the like.

Referring to FIGS. 15 and 16, the evaluation module 1610 may compare the velocity waveform 1600 (e.g., values of the monitored velocity of the blood flow in the carotid artery of a patient, or the like) to a first inflection threshold 1604. The first inflection threshold 1604 may correspond with a monitored velocity value (e.g., 45 cm/s, 80 cm/s, 90 cm/s, or the like). The evaluation module 1610 may identify a first inflection point 1602A with a velocity value greater than the first inflection threshold 1604. The first inflection point 1602A may correspond with the first heart sound (S1) at a first time interval. For instance, the first inflection point 1602A may correspond with the monitored velocity values decreasing in the velocity waveform 1600.

The evaluation module 1510 may compare the velocity waveform 1600 to a second heart sound threshold 1606. For instance, the second inflection threshold 1606 may have a smaller velocity value than the first inflection threshold 1604. In another example, the evaluation module 1510 may identify one or more of the inflection points 1602 with a value above the second inflection threshold 1606. In yet another example, the evaluation module 1510 may identify one or more of the inflection points 1602 between the first inflection threshold 1604 and the second inflection threshold 1606. For example, the evaluation module 1510 may identify a second inflection point 1602B with a velocity value greater than the second inflection threshold 1606. The second inflection point 1602 may correspond with velocity values increasing in the velocity waveform 1600. The evaluation module 1510 may identify a third inflection point 1602C. The third inflection point 1602C may have a velocity value greater than the second inflection threshold 1606. The third inflection point 1602C may correspond with the monitored velocity values decreasing in the velocity waveform 1600. The third inflection point may correspond with the second heart sound (S2) at a second time interval. Accordingly, the evaluation module 1510 may identify heart sounds using the velocity waveform 1600 provided by the ultrasonic transducer 1512. Thus, the blood filtration system 100 may determine the ejection time using the heart sounds of a patient, for instance to enhance the accuracy of determining the stroke volume of the patient.

Referring to FIG. 15, the evaluation module 1510 may determine physiological parameters of the patient including (but not limited to) cardiac power of the patient. For instance, the cardiac power of the patient may equal the cardiac output of the patient multiplied by the mean arterial pressure of the patient. In an example, the second sensor 126B may determine the mean arterial pressure of the patient. For example, the mean arterial pressure may be based on systolic pressure and diastolic pressure of a patient. The second sensor 126B may determine one or more of the systolic pressure (SP) or diastolic pressure (DP) of a patient. In an example, Equation 15 defines mean arterial pressure.

$$\text{Mean Arterial Pressure} = \frac{SP + 2(DP)}{3} \qquad \text{Equation 15}$$

In another example, the second sensor 126B may comprise a sphygmomanometer. The sphygmomanometer may facilitate measurement of the blood pressure of the patient, for instance the mean arterial pressure. The non-invasive sensors 1506 may include the sphygmomanometer (e.g, a blood pressure cuff, or the like). Thus, the blood filtration system may monitor pressure in vasculature of the patient using one or more of the invasive sensors 1504 or the non-invasive sensors 1506.

Referring to FIGS. 15 and 16, the evaluation module 1510 may determine physiological parameters of the patient including (but not limited to) carotid flow time. The carotid flow time may correspond with intravascular fluid volume status. In an example, the carotid flow time corresponds to the difference in time between the closing of the atrioventricular valves and the first heart sound (S1). For instance, the evaluation module 1510 may identify a fourth inflection point 1602D. The fourth inflection point 1602D may correspond with closing of atrioventricular valves. In another example, the fourth inflection point 1602D precedes the first inflection point 1602A. Accordingly, the blood filtration system may determine the carotid flow time of the patient using the ultrasonic transducer 1512.

Referring to FIG. 15, the evaluation module 1510 may determine one or more physiological parameters of the patient including (but not limited to) systemic vascular resistance ("SVR"). In an example, the SVR may change in correspondence with changes in viscosity of blood of the patient. Accordingly, changes in viscosity of blood may be a basis of change in the SVR. In another example, the SVR may change in correspondence with changes in geometry of vasculature of the patient. Thus, changes in geometry of vasculature may be a basis of change in the SVR.

In another example, the resistance to flow is governed by Equation 16 (Poiseuille's Law). Equation 16 includes flow rate (Q), radius (r), cylinder length (L), and blood viscosity (μ).

$$Q = \frac{(\Delta P) * \pi * r^4}{8 * L * \mu} \qquad \text{Equation 16}$$

Using Equation 16, vasculature of a patient may be approximated as a cylindrical tube. Algebraically manipulating Equation 16 yields Equation 17. Equation 17 includes the resistance to flow (R). The resistance to flow (R) may correspond with the SVR. For instance, the resistance to flow (R) may be associated with the resistance in a rigid cylinder. The SVR may be associated with the resistance of all blood vessels taken together. Accordingly, in an example, the resistance to flow (R) may equal the SVR.

$$R = \frac{8 * L * \mu}{\pi * r^4} \qquad \text{Equation 17}$$

Equation 17 shows the resistance to flow (R) may correspond with one or more of vasculature geometry (e.g., the radius of the vasculature) or the viscosity of blood (μ). Thus, the blood filtration system 100 may monitor the vasculature geometry or the viscosity of blood (μ) to correspondingly monitor the resistance to flow in the vasculature (or a rigid cylinder).

In an example, the blood viscosity (μ) may change in correspondence with the hematocrit value of the blood. For instance, Equation 18 approximates the relationship between the viscosity of blood (μ) and the hematocrit value of the blood (HCT). Equation 18 includes the viscosity of plasma (μp).

$$\mu = \mu p * (1 + 2.5 * HCT) \qquad \text{Equation 18:}$$

Referring to FIG. 15, the blood filtration system 100 may monitor the resistance to flow (or changes in resistance to flow) by monitoring the viscosity of blood. In an example, the physiological parameters may include one or more figures of merit. For instance, the evaluation module 1510 may determine the figures of merit based on the monitored physiological parameters. In an example, the evaluation module 1510 may determine a first figure of merit (Rv). The first figure of merit (Rv) may correspond with a first basis in change in the systemic vascular resistance of the patient. In an example, the first basis of change may correspond with changes in viscosity of blood (μ). In another example, the evaluation module 1510 may determine a second figure of merit (Rc). The second figure of merit (Rc) may correspond with a second basis in change in the systemic vascular resistance of the patient. In an example, the second basis of change may correspond with changes in vasculature geometry of the patient and changes in viscosity of blood (μ).

In an example, the first figure of merit (Rv) may correspond with a relative figure of viscosity based flow resistance. The first figure of merit (Rv) may include a ratio of the viscosity based flow resistance at a first time interval relative to the viscosity based flow resistance at a second time interval. For instance, the blood filtration system 100 may remove filtrate fluid from the blood of the patient between the first time interval and the second time interval. The viscosity of blood may change (e.g., increase, or the like) based on the removal of filtrate fluid from the blood between the first time interval and the second time interval. Equation 19 and Equation 20 define the viscosity based flow resistance values at the first and second time intervals (respectively).

$$R1 = \frac{8 * L * \mu 1}{\pi * r^4} \qquad \text{Equation 19}$$

$$R2 = \frac{8 * L * \mu 2}{\pi * r^4} \qquad \text{Equation 20}$$

Equation 21 defines the first figure of merit (Rv) as the ratio of the viscosity based flow resistance at a first time interval relative to the viscosity based flow resistance at a second time interval. In another example, the first figure of merit (Rv) corresponds with a change in resistance due to changes in viscosity. In an example, Equation 21 may assume there is no change in vessel geometry.

$$Rv = \frac{R1}{R2} = \frac{1 + 2.5 * HCT1}{1 + 2.5 * HCT2} \qquad \text{Equation 21}$$

In another example, the second figure of merit (Rc) may correspond with a relative figure of composite flow resistance. Composite flow resistance may correspond to the SVR. The second figure of merit (Rc) may include a ratio of the composite flow resistance at the first time interval (SVR1) relative to the composite flow resistance at the second time interval (SVR2). In another example, the second figure of merit (Rv) corresponds with a change in resistance due to changes in both viscosity and vessel geometry (e.g., changes due to vasoconstriction, vasodilation, or the like). Equation 22 defines the second figure of merit (Rc).

$$Rc = \frac{SVR1}{SVR2} \qquad \text{Equation 22}$$

The evaluation module 1510 may determine a third figure of merit (Rz) based on the monitored physiological parameters. In an example, the third figure of merit (Rz) may also be referred to as a Zvicon number, Vicon number, or the like. The third figure of merit (Rz) may include a ratio of the first figure of merit (Rv) to the second figure of merit (Rc). The third figure of merit (Rz) may include the first figure of merit (Rv) divided the second figure of merit (Rc). Accordingly, the third figure of merit (Rz) may include a ratio of change in resistance due to changes in viscosity in relation to changes in resistance due to vessel geometry and viscosity. Thus, the third figure of merit (Rz) may correspond with a relative change in resistance due to viscosity. For instance, the third figure of merit (Rz) may correspond with the change in resistance due to viscosity relative to a change in resistance due to changes in vessel geometry. Equation 23 defines the third figure of merit (Rz).

$$Rz = \frac{Rv}{Rc} = \frac{SVR1}{SVR2} * \left( \frac{1 + 2.5 * HCT1}{1 + 2.5 * HCT2} \right) \qquad \text{Equation 23}$$

As described herein, the evaluation module 1510 may determine the SVR of the patient. For instance, the evaluation module 1510 may cooperate with the one or more sensors 126 to determine the SVR of the patient. Accordingly, the evaluation module may determine the composite flow resistance at the first time interval (SVR1) and the composite flow resistance at the second time interval (SVR2). Thus, Equation 23 may be algebraically manipulated to yield Equation 24.

$$Rz = \left( \frac{CO2}{MAP2 - CVP2} \right) * \left( \frac{MAP1 - CVP1}{CO1} \right) * \left( \frac{1 + 2.5 * HCT2}{1 + 2.5 * HCT1} \right) \qquad \text{Equation 24}$$

The blood filtration system may monitor physiological parameters including (but not limited to) one or more of cardiac output, mean arterial, central venous pressure, or hematocrit. Accordingly, the evaluation module may determine the third figure of merit (Rz) using the monitored physiological parameters. For instance, the evaluation module may use values of the physiological parameters at the first time interval and the second time interval to determine the third figure of merit (Rz).

The system 100 may present the one or more figures of merit (e.g., Rv, Rc, Rz, or the like) on the display 202. In an example, the evaluation module 1510 may cooperate with the display module 200 to include the figures of merit in the diagnostic matrix 204. In another example, a user may observe the figures of merit, for instance to determine changes in SVR based on viscosity or changes in SVR based on vessel geometry. In an example where the viscosity of blood does not change between the first time interval and the second time, the first figure of merit (Rv) may equal 1. Accordingly, a user may determine the resistance change based on changes in vessel geometry where the third figure of merit (Rz) has a value other than 1 and the first figure of merit (Rv) has a value of 1. In another example where the viscosity of blood changes between the first time interval and the second time interval, the first figure of merit (Rv) may have a value other than 1. Thus, a user may determine the resistance changed based on changes in viscosity. In another example, the user may compare the third FIG. 15 of merit (Rz) with a range of values to determine whether the SVR changed based on viscosity or changed based on vessel geometry.

In another example, the evaluation module 1510 may determine physiological parameters of the patient including (but not limited to) oxygen consumption of the patient (VO2). In an example, Equation 19 describes the relationship between hemoglobin concentration (Hb), oxygen consumption (VO2), arterial oxygen saturation (SpO2), venous oxygen saturation (SvO2), and cardiac output (CO). The hemoglobin concentration may correspond with the hematocrit value. Equation 25 may correspond with the Fick equation. Equation 25 may include a constant (c).

$$VO2 = (c)(CO)(SpO2 - SvO2)(Hb) \qquad \text{Equation 25:}$$

Equation 19 may be algebraically manipulated to provide Equation 26:

$$SvO2 = SpO2 - \left( \frac{(c)(VO2)}{CO * [Hb]} \right) \qquad \text{Equation 26}$$

In an example where a patient is hypervolemic with attendant hemodilution, the hematocrit value of the patient may be lower than normal. Accordingly, the SvO2 may decrease. In another example, a reduction in cardiac output, a decrease in SpO2, or an increase in oxygen consumption may correspondingly decrease the SvO2 of the patient. Thus, the SvO2 may change in correspondence with one or more of hematocrit value, cardiac output, SpO2, oxygen consumption, or the like. Accordingly, the blood filtration system may monitor physiological parameters of the patient, including (but not limited to) hematocrit value, cardiac output, SpO2, SvO2, oxygen consumption, or the like Referring to FIG. 15, the evaluation module 1510 may determine physiological parameters of the patient including (but not limited to) extracellular fluid volume (ECFV), intracellular fluid volume, or total fluid volume. Equation 27 is the ratio of extracellular fluid volume (ECFV) to total fluid volume (TFV). The total fluid volume equals the extracellular fluid volume plus the intracellular fluid volume.

$$\frac{ECFV}{TFV} = \frac{ECFV}{EXCF + ICFV} \qquad \text{Equation 27}$$

The blood filtration system 100 may determine the ratio of extracellular fluid volume (ECFV) to total fluid volume (TFV). For instance, the ratio of extracellular fluid volume (ECFV) to total fluid volume (TFV) may be determined with the impedance sensor 1500. In another example, the total fluid volume may be referred to as total body water. In an example, the impedance sensor 1500 may use different frequencies to determine the ratio of extracellular fluid volume (ECFV) to total fluid volume (TFV). Higher frequencies (e.g., 90 kHz, 120 kHz, 150 kHz, or the like) may penetrate cell membranes and thus account for intracellular and extracellular fluid. In some examples, lower frequencies (e.g., 2 kHz, 5 kHz, 15 kHz, or the like) may not penetrate cell membranes. Accordingly, the lower frequencies may account only for extracellular fluid (e.g., in the interstitial tissue, vascular systems, or the like). Thus, the ratio expressed in Equation 27 may provide a physiological parameter corresponding to fluid imbalance of a patient.

In yet another example, the ratio of extracellular fluid volume (ECFV) to total fluid volume (TFV) may correspond with excessive extracellular fluid volume. For instance, an increase in the ratio may correspond with an increase in extracellular fluid volume (ECFV). In another example, a patient may have excessive extracellular fluid volume (ECFV) if the ratio exceeds a specified threshold. In yet another example, the ratio may help determine a difference between excessive extracellular fluid volume and excessive intravascular fluid volume. For instance, a user may determine whether a patient is experiencing hypervolemia or increased interstitial fluid by monitoring the ratio of extracellular fluid volume (ECFV) to total fluid volume (TFV) or the hematocrit value of the patient.

Referring to FIG. 15, the blood filtration system may provide a suggested corrective action 1514. The suggested corrective action 1514 may include suggestions to a user for operation of the blood filtration system. In an example, the content presented on the display 202 may include the suggested corrective action 1514. The system 100 may determine the suggested corrective action based on the monitored physiological parameters of the patient. For instance, the controller 102 may include a therapy guidance module 1516. The therapy guidance module 1516 may determine the suggested corrective action 1514. For example, the therapy guidance module 1510 may monitor physiological parameters of the patient to determine the suggested corrective action 1514. In an example, the suggested corrective action 1514 may facilitate maintenance of the diagnostic point 206 within the zone of stability 210.

In another example, the therapy guidance module 1516 may compare the monitored hematocrit value with a hematocrit value range. In an example, the hematocrit value range may extend between a first hematocrit value and a second hematocrit value. The therapy guidance module 1516 may provide the suggested corrective action 1514 based on the comparison of the monitored hematocrit with the hematocrit value range. For example, the suggested corrective action 1514 may include a suggestion (e.g, a message including text, or the like) to reduce a filtration rate when the hematocrit value is outside the hematocrit value range. In another example, the suggested corrective action 1514 may include increasing the filtration rate when the hematocrit value is within the hematocrit value range. In yet another example, the suggested corrective action 1514 may include changing (e.g., increasing, decreasing, or the like) the blood flow rate (corresponding to a speed of the blood pump 112, shown in FIG. 1) based on the comparison of the SvO2 with the SvO2 value range.

The therapy guidance module 1516 may compare the monitored SvO2 with a SvO2 value range. For instance, the SvO2 value range may extend between a first SvO2 value and a second SvO2 value. The therapy guidance module 1516 may provide the suggested corrective action 1514 based on the comparison of the monitored SvO2 with the SvO2 value range. In an example, the suggested corrective action 1514 may include a suggestion to reduce the filtration rate when the SvO2 is outside the SvO2 value range. In another example, the suggested corrective action 1514 may include increasing the filtration rate when the SvO2 is within the SvO2 value range. In yet another example, the suggested corrective action 1514 may include changing (e.g., increasing, decreasing, or the like) the blood flow rate (corresponding to a speed of the blood pump 112, shown in FIG. 1) based on the comparison of the SvO2 with the SvO2 value range.

The suggested corrective action 1514 may include increasing the filtration rate when the hematocrit is within the hematocrit value range and the SvO2 is within the SvO2 value range. The suggested corrective action 1514 may include decreasing a filtration rate when the hematocrit is outside the hematocrit value range and the SvO2 is within the SvO2 value range. The suggested correction action 1514 may include setting the filtration rate to zero in correspondence with the hematocrit value outside the hematocrit value range and the SvO2 outside the SvO2 value range. Accordingly, the blood filtration system 100 may provide the suggested corrective action 1514 based on the monitored physiological parameters.

In yet another example, the system 100 may wait for a specified time period before providing the suggested correction 1514. The therapy guidance module 1516 may wait to allow the physiological parameters of the patient to equalize (e.g., normalize, settle, or the like). For instance, the therapy guidance module 1516 may wait to allow for physiological parameters to equalize after changing one or more of a blood flow rate or a filtration rate of the blood filtration system 100. In another example, the controller 102 may implement the suggested corrective action 1514. For instance, the therapy guidance module 1516 may implement the suggested corrective action 1514. In another example, the controller 102 waits for a specified time period to implement the suggested corrective action. For example, the display 202 may present the suggested corrective action 1514 for the specified time period. The therapy guidance module 1516 may implement the suggested corrective action 1514 at the expiration of the specified time period. For instance, the therapy guidance module may set the filtration rate to zero in correspondence with the hematocrit value outside the hematocrit value range and the SvO2 outside the SvO2 value range. Thus, the blood filtration system 100 may implement the suggested corrective action 1514.

Figure 17:
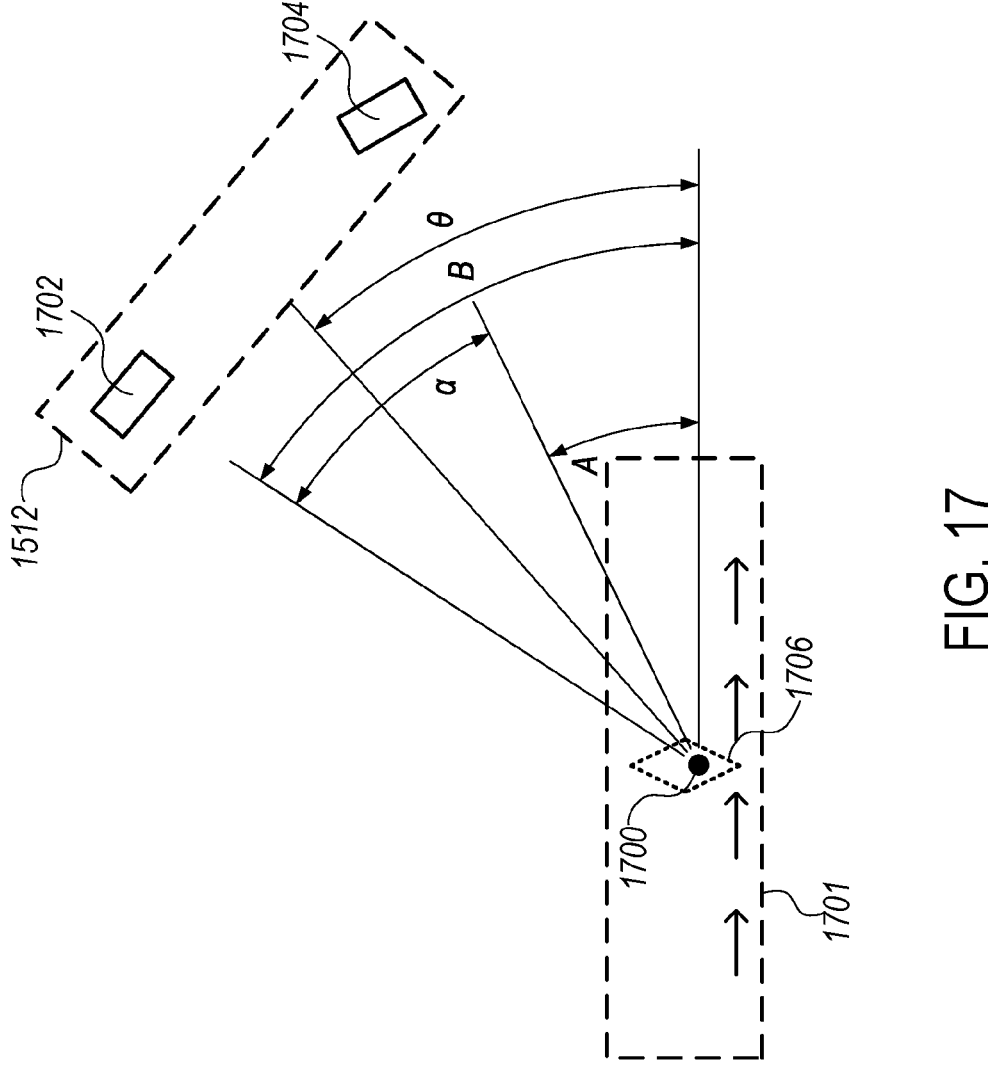
FIG. 17 shows a schematic diagram of an ultrasonic transducer.

FIG. 17 shows a schematic diagram of an ultrasonic transducer, for instance the ultrasonic transducer 1512. The ultrasonic transducer 1512 may facilitate determining the velocity of blood in the vein 1701. For instance, a red blood cell 1200 is a constituent of blood in the vein 1701. FIG. 10 shows the direction of movement for the red blood cell 1700 through the vein 1701 with dashed arrows. The red blood cell 1700 scatters waves generated by the ultrasonic transducer 1512, and the ultrasonic transducer 1512 may determine the velocity of the red blood cell 1700 (flowing in the blood) based on the scattering of the waves by the red blood cell 1700.

In an example, the ultrasonic transducer 1512 includes a transmitter 1702 and a receiver 1704. The transmitter 1702 may generate a signal, for instance an ultrasonic wave, and the transmitter 1702 transmits the signal through the blood in the vein 1701 (shown in FIG. 10). The signal is scattered by constituents of the blood, for instance the red blood cell 1700. The scattered signal may be received by the receiver 1704. The ultrasonic transducer 1512 may determine the velocity of the red blood cell 1700 using the scattered signal received by the receiver 1704.

For example, the velocity of the red blood cell 1700 flowing through the vein 1701 may be determined according to the following equations including the variables: velocity of the red blood cell 1700 (v), speed of sound in blood (c), the frequency of the signal transmitted by the transmitter 1702 ($f_o$), the Doppler shifted frequency of the signal transmitted by the transmitter 1702 (f'), the angle between a longitudinal axis of the vein 1701 and the transducer direction ($\Theta$), and The Doppler shift frequency ($f_d$) is equal to the difference between $f_o$ and f'. Equation 28 is the Doppler shift equation and includes the following variables: the velocity of sound ($V_c$), velocity of observer ($V_{ob}$), and the velocity of source of emitted sound waves ($V_s$).

$$f' = f_o\left[\frac{v_c \pm v_{ob}}{v_c + v_s}\right] \qquad \text{Equation 28}$$

Applying Equation 28 to the ultrasonic transducer 1512 and the red blood cell 1700 (shown in FIG. 12) yields Equation 29:

$$f' = f_o\left[\frac{c - v\cos A}{c + v\cos B}\right] \qquad \text{Equation 29}$$

Equations 30 and 31 relate angles A, B, $\theta$, and $\alpha$:

$$A = \theta - \frac{\alpha}{2} \qquad \text{Equation 30}$$

$$B = \theta - \frac{\alpha}{2} \qquad \text{Equation 31}$$

Substituting Equations 30 and 31 into Equation 29 yields Equation 32:

$$f' = f_o\left|\frac{c - v\cos\left(\theta - \frac{\alpha}{2}\right)}{c + v\cos\left(\theta + \frac{\alpha}{2}\right)}\right| \qquad \text{Equation 32}$$

As described herein, the Doppler shift frequency ($f_d$) is equal to the difference between $f_o$ and f':

$$f_d = f' - f_o \qquad \text{Equation 33:}$$

Substituting Equation 32 into Equation 33 yields Equation 34:

$$f_d = f_o\left[\frac{c - v\cos\left(\theta - \frac{\alpha}{2}\right) - c - v\cos\left(\theta + \frac{\alpha}{2}\right)}{c + v\cos\left(\theta + \frac{\alpha}{2}\right)}\right] \qquad \text{Equation 34}$$

Algebraically manipulating Equation 34 yields Equation 35:

$$f_d = f_o(-v)\left[\frac{\cos\left(\theta + \frac{\alpha}{2}\right) + \cos\left(\theta - \frac{\alpha}{2}\right)}{c + v\cos\left(\theta + \frac{\alpha}{2}\right)}\right] \qquad \text{Equation 35}$$

Equation 35 may be algebraically manipulated to yield Equation 36:

$$f_d = \left[\frac{-2f_o v}{c}\right]\left[\frac{\cos(\theta)\cos\left(\frac{\alpha}{2}\right)}{1 + \frac{v}{c}\cos\left(\theta + \frac{\alpha}{2}\right)}\right] \qquad \text{Equation 36}$$

Algebraically manipulating Equation 36 yields Equation 37:

$$|f_d| \cong \left[\frac{2f_o v}{c}\right]\left[\cos(\theta)\cos\left(\frac{\alpha}{2}\right)\right] \qquad \text{Equation 37}$$

Assuming $\alpha$ is a small value in Equation 37 yields Equation 38:

$$|f_d| \cong \left[\frac{2f_o v}{c}\right][\cos(\theta)] \qquad \text{Equation 38}$$

Equation 38 may be algebraically manipulated to determine the velocity of the red blood cell 1700 (v) in Equation 39:

$$v \cong \frac{|f_d|c}{2f_o[\cos\theta]} \qquad \text{Equation 39}$$

Referring to FIG. 17, the ultrasonic transducer 1512 may measure the velocity of blood within a focal zone 1706. In an example, the focal zone 1706 may correspond with a region where emitted and reflected ultrasonic signals coincide with each other. For instance, the focal zone 1706 may be located within the vein 1701. In another example, the focal zone 1706 may be proximate a center of the vein 1701. In yet another example, the focal zone 1706 may be remove from walls of the vein 1701. In still yet another example, the focal zone 1706 may be remote from a catheter inserted into the vein 1701. Accordingly, the velocity of the red blood cell 1700 may be detected in correspondence with the red blood cell 1700 located in the focal zone 1706.

Figure 18A:
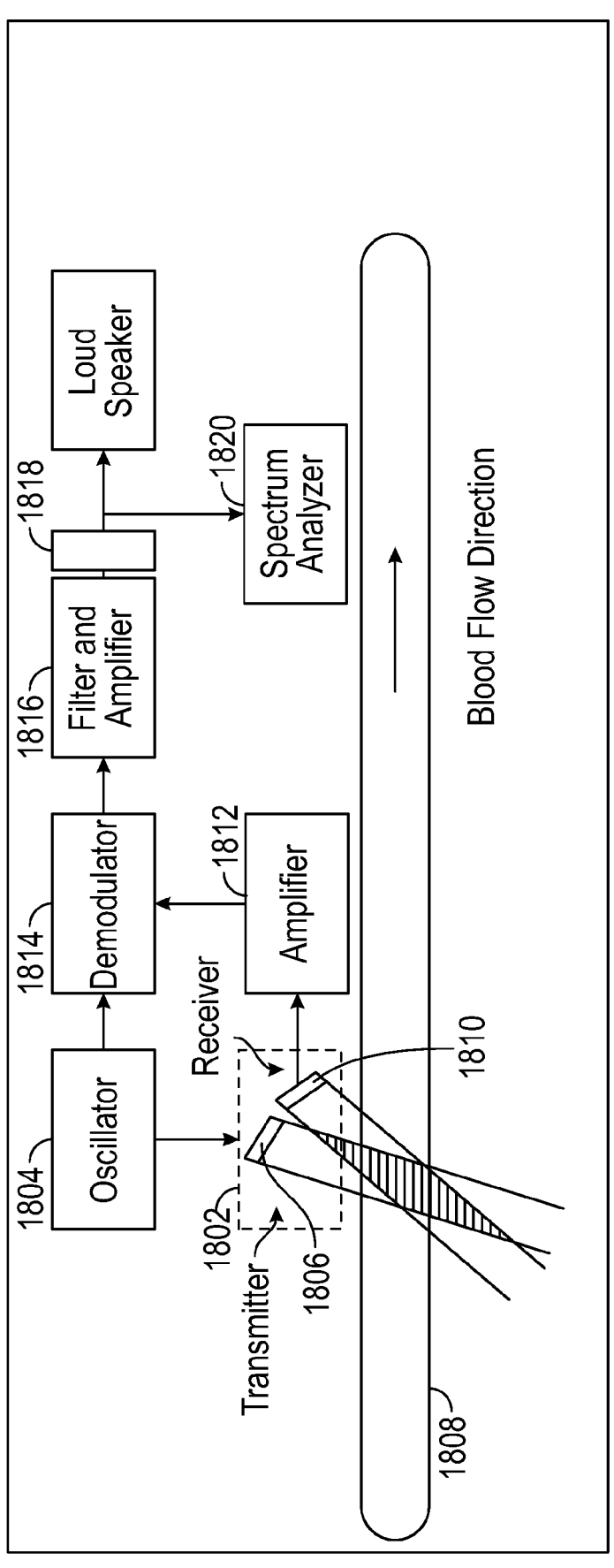
FIG. 18A shows a schematic diagram of a blood filtration system including a non-directional (e.g., unidirectional) Doppler transducer.

FIG. 18A shows a schematic diagram of a blood filtration system 1800 including a non-directional (or unidirectional) Doppler transducer 1802. In an example, oscillator 1804 drives a transmitter 1806 to transmit ultrasonic waves that interact with blood (e.g., red blood cells in the blood, or the like) in vasculature 1808 (e.g., the vein 1701 shown in FIG. 17, an artery, or the like). For instance, the transmitter 1806 transmits ultrasonic waves to determine the velocity of blood in the vasculature 1808.

The non-directional Doppler transducer 1802 may include a receiver 1810. The receiver 1810 may receive scattered ultrasonic waves that interact with blood (e.g., the red blood cell 1700 shown in FIG. 17, or the like). The receiver 1810 may communicate the received signals to a first amplifier 1812. The amplifier 1812 may be in communication with a demodulator 1814. The demodulator 1814 may communicate with the oscillator 1804 and the amplifier 1812 to demodulate the signals received at the receiver 1810.

The system 1800 may transmit the demodulated signal to one or more of a filter 1816 or a second amplifier 1818. For instance, the second amplifier 1818 may amplify the demodulated signal that has passed through the filter 1816. In an example, the demodulated signal may be analyzed with a spectrum analyzer 1820, for instance to determine the Doppler shift frequency. In yet another example, the system 1800 uses the non-directional Doppler transducer 1802 to distinguish between flow in a vein (e.g., blood flowing in a first portion of vasculature in a first direction, or the like) and flow in an artery (e.g., blood flowing in a second portion of vasculature in a second direction). For example, the system 1800 may monitor the DC offset of the demodulated signal (e.g., with the spectrum analyzer 1820, or the like) to determine the flow rate through the vein (e.g., vasculature 1808, or the like). In another example, the system 1800 may monitor the time varying component of the demodulated signal to determine the flow rate through the artery. Accordingly, the system 1800 is able to determine if the non-directional Doppler transducer 1802 has insonated one or more of a vein or an artery. Thus, performance of the system 1800 may be enhanced by enhancing the accuracy of measured flow in the vasculature 1808 of a patient.

Figure 18B:
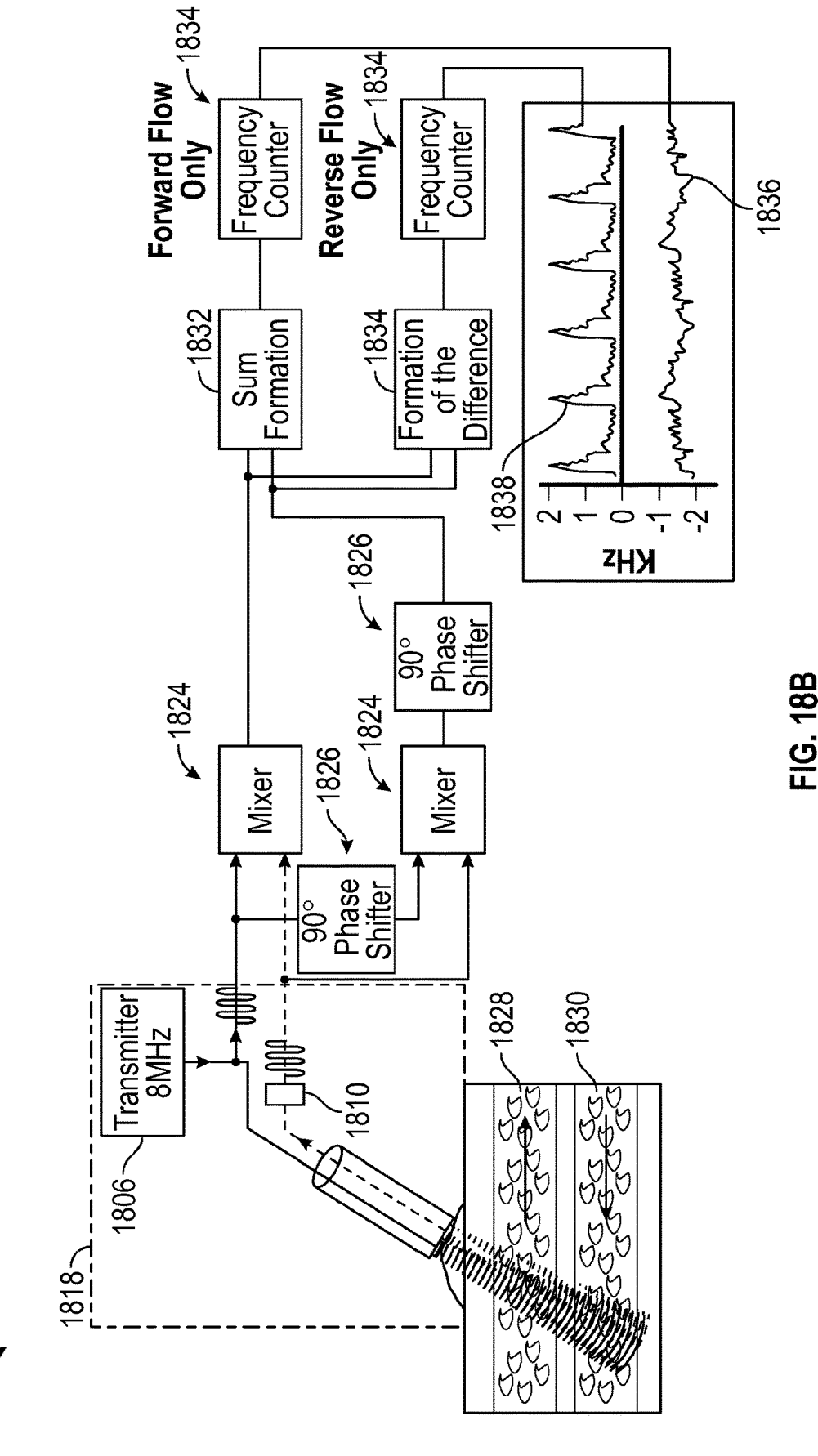
FIG. 18B shows a schematic diagram of another example of the blood filtration system including a directional (e.g., bi-directional) Doppler transducer.

FIG. 18B shows a schematic diagram of another example of the blood filtration system 1800 including a directional (e.g., bi-directional) Doppler transducer 1822. The directional Doppler transducer 1822 may include the transmitter 1806 and the receiver 1810. The receiver 1810 may transmit a signal corresponding to the received ultrasonic waves to one or more mixers 1824. In another example, the receiver 1810 may transmit the signal corresponding to the received ultrasonic waves to one or more phase shifters 1826. The mixers 1824 and the phase shifters 1826 may cooperate to condition the signal received from the receiver 1810. For example, the mixers 1824 and phase shifters 1826 may cooperate to condition received signals to determine the velocity of flow in the vasculature 1808 of the patient.

In another example, the system 1800 may use the directional Doppler transducer 1822 to distinguish between flow in a vein 1828 and flow in an artery 1830. In an example, the artery 1830 is proximate the vein 1828. Accordingly, in some examples, the directional Doppler transducer 1822 insonates both the vein 1828 and the vein 1330. The insonation of both the vein 1828 and the artery 1830 attenuates the ultrasonic waves, and the receiver 1810 receives the attenuated ultrasonic waves. Accordingly, the receiver 1810 receives a signal corresponding to flow in both the vein 1828 and the artery 1830. Thus, the system 1800 uses the directional Doppler transducer 1822 to distinguish between the flow in the vein 1828 and the flow in the artery 1830.

For example, the system 1800 uses a summation block 1832 to determine the sum (e.g., using mathematical addition, or the like) of conditioned signals that were received at the receiver 1810. The system 1800 may communicate the sum to one or more frequency counters 1834. For instance, the frequency counters 1834 may determine a vein flow signal 1836 corresponding to the flow in the vein 1828 (shown with an arrow in a first direction in FIG. 18B). The sum of the conditioned signals may correspond to flow in the vein 1828.

In another example, the system 1800 uses a difference block to determine the difference (e.g., using mathematical subtraction, or the like) between the conditioned signals that were received at the receiver 1810. The system 1800 may communicate the difference to the frequency counters 1834. For instance, the frequency counters 1834 may determine an artery flow signal 1838 corresponding to the flow in the artery 1830 (shown with an arrow in a second direction in FIG. 18B). The difference between the conditioned signals may correspond to flow in the artery 1830. Accordingly, the system 1800 uses the directional Doppler transducer 1822 to distinguish between flow in the vein 1828 and flow in the artery 1830. Thus, accuracy and precision of venous flow rate determinations are enhanced because the system 1800 may distinguish between flow in the vein 1828 and flow in the artery 1830.

FIG. 19 shows one example of a method 1900 for operating a blood filtration system, including one or more of the blood filtration system 100 described herein. In describing the method 1900, reference is made to one or more components, features, functions and operations previously described herein. Where convenient, reference is made to the components, features, operations and the like with reference numerals. The reference numerals provided are exemplary and are not exclusive. For instance, components, features, functions, operations and the like described in the method 1900 include, but are not limited to, the corresponding numbered elements provided herein and other corresponding elements described herein (both numbered and unnumbered) as well as their equivalents.

The method 1900 may include at 1902 determining a filtration value corresponding to an amount of filtrate fluid removed from the blood of a patient. The filtrate fluid may include one or more plasma constituents of the blood. At 1904, the method 1900 may include determining a total body water (TBW) value of the patient. The method 1900 includes at 1906 that determining the TBW value may include monitoring an impedance value of a portion of a body of the patient using an impedance sensor 1500. The method 1900 includes at 1908 that determining the TBW value may include determining the TBW value based on the monitored impedance value. At 1910, the method 1900 may include correcting the TBW based on the amount of filtrate fluid removed from the blood of the patient.

Several options for the method 1900 follow. Correcting the TBW value may include determining a first TBW value, for example at a first time interval. Correcting the TBW value may include determining a second TBW value, for instance at a second time interval. Correcting the TBW value may include determining a TBW difference corresponding to a difference between the first TBW value and the second TBW value. Correcting the TBW may include comparing the TBW difference to the filtration value to determine an error therebetween. Correcting the TBW value may include applying a correction to the monitored impedance value based on the error. In another example, the system 100 may use the corrected TBW to determine a ratio of extracellular fluid volume to the TBW.

VARIOUS NOTES & ASPECTS

Example 1 is a blood filtration system, comprising: one or more sensors configured to determine one or more physiological parameters including venous oxygen saturation (SvO2) and hematocrit of a patient; a controller in communication with the one or more sensors, wherein: the controller is configured to monitor the physiological parameters using the sensors; and the controller includes a display module configured to generate content; and a display configured for presenting the content including a diagnostic matrix having a diagnostic point, wherein the display module is configured to change the diagnostic point within the diagnostic matrix according to changes in the monitored physiological parameters.

In Example 2, the subject matter of Example 1 optionally includes wherein: the display module is configured to determine a zone of stability associated with the monitored physiological parameters; and the zone of stability includes one or more value ranges for the physiological parameters.

In Example 3, the subject matter of Example 2 optionally includes wherein the display is configured to present the diagnostic matrix and the zone of stability.

In Example 4, the subject matter of any one or more of Examples 1-3 optionally include wherein: the controller includes a therapy guidance module configured to determine a suggested corrective action based on the monitored physiological parameters.

In Example 5, the subject matter of Example 4 optionally includes wherein the display is configured to present the suggested corrective action, the diagnostic point, and a zone of stability.

In Example 6, the subject matter of any one or more of Examples 4-5 optionally include wherein the suggested corrective action includes changes in an extraction rate of filtrate fluid from blood of a patient.

In Example 7, the subject matter of Example 6 optionally includes wherein the display is configured to display the suggested corrective action and the diagnostic matrix.

In Example 8, the subject matter of any one or more of Examples 4-7 optionally include wherein: the therapy guidance module is configured to compare the monitored hematocrit with a hematocrit value range, the hematocrit value range extending between a first hematocrit value and a second hematocrit value; the controller is configured to provide the suggested corrective action based on the comparison of the monitored hematocrit with the hematocrit value range.

In Example 9, the subject matter of Example 8 optionally includes wherein: the controller includes a comparator configured to compare the monitored SvO2 with a SvO2 value range, the SvO2 value range extending between a first SvO2 value and a second SvO2 value; the controller is configured to provide the suggested corrective action based on the comparison of the monitored SvO2 with the SvO2 value range.

In Example 10, the subject matter of Example 9 optionally includes value range.

In Example 11, the subject matter of any one or more of Examples 9-10 optionally include value range.

In Example 12, the subject matter of any one or more of Examples 9-11 optionally include value range.

In Example 13, the subject matter of Example 12 optionally includes wherein the controller is configured to wait for a specified time period before providing the suggested correction.

In Example 14, the subject matter of any one or more of Examples 9-13 optionally include value range.

In Example 15, the subject matter of any one or more of Examples 9-14 optionally include value range.

In Example 16, the subject matter of any one or more of Examples 1-15 optionally include wherein the physiological parameters include one or more of relative blood volume, absolute blood volume, plasma volume, oxygen extraction ratio, ejection time, stroke volume, carotid flow time, cardiac output, cardiac power, central venous pressure, mean arterial pressure, systemic vascular resistance, heart rate, respiratory rate, cardiac power, hemoglobin concentration, extracellular fluid volume, or thoracic fluid content.

In Example 17, the subject matter of Example 16 optionally includes wherein the controller includes an evaluation module configured to determine the physiological parameters using the one or more sensors.

In Example 18, the subject matter of any one or more of Examples 11-17 optionally include wherein the display module is configured to change a size of the diagnostic point in correspondence with changes in one or more of the monitored parameters.

In Example 19, the subject matter of Example 18 optionally includes wherein the display module is configured to change a color of the diagnostic point in correspondence with changes in one or more of the monitored parameters.

In Example 20, the subject matter of any one or more of Examples 11-19 optionally include wherein the display module is configured to change a color of the diagnostic point in correspondence with changes in one or more of the monitored parameters.

In Example 21, the subject matter of any one or more of Examples 11-20 optionally include wherein the display module is configured to move the diagnostic point along one or more axis, the one or more axis corresponding with values of the monitored diagnostic parameters.

In Example 22, the subject matter of any one or more of Examples 11-21 optionally include wherein the physiological parameters comprise hemodynamic parameters that affect hemodynamic stability of the patient.

In Example 23, the subject matter of any one or more of Examples 11-22 optionally include wherein the controller is configured to determine a systemic vascular resistance (SVR) of the patient using the monitored physiological parameters.

In Example 24, the subject matter of Example 23 optionally includes wherein: the one or more sensors comprise at least one pressure sensor in communication with vasculature of the patient; and the at least one pressure sensor is configured to determine pressure in the vasculature of the patient.

In Example 25, the subject matter of Example 24 optionally includes wherein the controller uses the pressure in the vasculature to determine the SVR.

In Example 26, the subject matter of Example 25 optionally includes wherein: the one or more sensors comprise at least one hematocrit sensor configured to determine a hematocrit value of the patient.

In Example 27, the subject matter of any one or more of Examples 23-26 optionally include wherein: the one or more sensors comprise at least one hematocrit sensor configured to determine a hematocrit value of the patient.

In Example 28, the subject matter of Example 27 optionally includes wherein the controller uses the hematocrit value to determine the SVR.

In Example 29, the subject matter of any one or more of Examples 23-28 optionally include wherein: the controller determines a first figure of merit corresponding to first basis of change in the SVR; and the controller determines a second figure of merit corresponding to a second basis of change in the SVR.

In Example 30, the subject matter of Example 29 optionally includes wherein: the controller determines a third figure of merit corresponding to a ratio of the first figure of merit to the second figure of merit.

In Example 31, the subject matter of any one or more of Examples 29-30 optionally include wherein the first basis of change in the SVR corresponds with changes in viscosity of the blood of the patient.

In Example 32, the subject matter of Example 31 optionally includes wherein the second basis of change in the SVR corresponds with changes in vasculature geometry.

In Example 33, the subject matter of any one or more of Examples 29-32 optionally include wherein the second basis of change in the SVR corresponds with changes in vasculature geometry.

In Example 34, the subject matter of any one or more of Examples 29-33 optionally include wherein the first basis of change in the SVR corresponds with changes in a hematocrit value of a patient.

In Example 35, the subject matter of any one or more of Examples 29-34 optionally include wherein the second basis of change in the SVR corresponds with changes in a hematocrit value of a patient.

In Example 36, the subject matter of any one or more of Examples 29-35 optionally include wherein the display is configured to present the first figure of merit and the second figure of merit.

In Example 37, the subject matter of any one or more of Examples 23-36 optionally include wherein: the SVR equals a first quantity divided by a second quantity; the first quantity equals a difference between a mean arterial pressure of a patient and a central venous pressure of the patient; the second quantity equals a cardiac output of the patient.

Example 38 is a blood filtration system configured to remove one or more plasma constituents from blood of a patient, the blood filtration system comprising: a pressure sensor configured for communication with vasculature of a patient; wherein the pressure sensor is configured to determine pressure in the vasculature; an impedance sensor configured for communication with a thorax of the patient, the impedance sensor configured to determine the impedance of the thorax; a controller in communication with the pressure sensor and the impedance sensor, wherein: the controller is configured to monitor the pressure in the vasculature and the impedance of the thorax; and the controller is configured to determine one or more physiological parameters including a systemic vascular resistance of the patient, wherein the controller uses the pressure in the vasculature and the impedance of the thorax to determine the systemic vascular resistance of the patient.

In Example 39, the subject matter of Example 38 optionally includes wherein the pressure sensor is configured for invasive communication with the vasculature of the patient and the impedance sensor is configured for non-invasive communication with the thorax of the patient.

In Example 40, the subject matter of any one or more of Examples 38-39 optionally include wherein: the physiological parameters include one or more of ejection time, stroke volume, cardiac output, heart rate, respiratory rate, cardiac power, or thoracic fluid content; and the controller is configured to determine the physiological parameters using at least one of the monitored pressure in the vasculature or the impedance of the thorax.

In Example 41, the subject matter of any one or more of Examples 38-40 optionally include wherein: the controller is configured to determine an ejection time corresponding to a duration of ventricular ejection of the patient; and the controller determines the ejection time based on the impedance of the thorax.

In Example 42, the subject matter of Example 41 optionally includes wherein the controller is configured to determine a stroke volume using the ejection time.

In Example 43, the subject matter of Example 42 optionally includes wherein: the physiological parameters include one or more of resistivity of the blood, impedance of the blood, impedance of the thorax, or total body impedance; and the controller determines the stroke volume based on one or more of the resistivity of the blood, impedance of the blood, or total body impedance.

In Example 44, the subject matter of any one or more of Examples 42-43 optionally include wherein the controller is configured to determine a cardiac output of the patient based on the stroke volume.

In Example 45, the subject matter of any one or more of Examples 43-44 optionally include wherein: the physiological parameters include a heart rate of the patient; the controller is configured to determine the heart rate of the patient based on the impedance of the thorax; and the controller is configured to determine cardiac output of the patient based on the heart rate of the patient.

In Example 46, the subject matter of any one or more of Examples 44-45 optionally include wherein the controller is configured to determine the systemic vascular resistance based on the cardiac output.

In Example 47, the subject matter of Example 46 optionally includes wherein: the pressure sensor comprises a first pressure sensor and a second pressure sensor; the controller is configured to determine a mean arterial pressure of the patient using the first pressure sensor; the second pressure sensor is configured for communication with a catheter inserted into the vasculature of the patient; and the controller is configured to determine a central venous pressure of the patient using the second pressure sensor; and the controller is configured to determine the systemic vascular resistance based on one or more of the mean arterial pressure, the central venous pressure, or the cardiac output.

In Example 48, the subject matter of any one or more of Examples 38-47 optionally include wherein the pressure sensor comprises a first pressure sensor, and the controller is configured to determine a mean arterial pressure of the patient using the first pressure sensor.

In Example 49, the subject matter of Example 48 optionally includes wherein the first pressure sensor includes a sphygmomanometer.

In Example 50, the subject matter of any one or more of Examples 48-49 optionally include wherein: the pressure sensor comprises the first pressure sensor and a second pressure sensor; the second pressure sensor is configured for communication with a catheter inserted into the vasculature of the patient; and the controller is configured to determine a central venous pressure of the patient using the second pressure sensor.

In Example 51, the subject matter of Example 50 optionally includes wherein the first pressure sensor is configured for non-invasive communication with the vasculature of the patient and the second pressure sensor is configured for invasive communication with the vasculature of the patient.

In Example 52, the subject matter of Example 51 optionally includes wherein the controller is configured to determine the systemic vascular resistance based on one or more of the mean arterial pressure or the central venous pressure.

In Example 53, the subject matter of any one or more of Examples 38-52 optionally include wherein: the pressure sensor comprises a first pressure sensor, and the controller is configured to determine a central venous pressure of the patient using the first pressure sensor; and the controller is configured to determine the systemic vascular resistance based on the central venous pressure.

Example 54 is a method of operating a blood filtration system, the method comprising: determining a filtration value corresponding to an amount of filtrate fluid removed from the blood of a patient, wherein the filtrate fluid includes one or more plasma constituents of the blood; and determining a total body water (TBW) value of the patient, determining the TBW value including: monitoring an impedance value of a portion of a body of the patient using an impedance sensor; determining the TBW value based on the monitored impedance value; and correcting the TBW based on the amount of filtrate fluid removed from the blood of the patient.

In Example 55, the subject matter of Example 54 optionally includes wherein correcting the TBW value includes: determining a first TBW value; determining a second TBW value; determining a TBW difference corresponding to a difference between the first TBW value and the second TBW value; comparing the TBW difference to the filtration value to determine an error therebetween; and applying a correction to the monitored impedance value based on the error.

In Example 56, the subject matter of any one or more of Examples 54-55 optionally include determining a ratio of extracellular fluid volume to the TBW.

Each of these non-limiting aspects can stand on its own, or can be combined in various permutations or combinations with one or more of the other aspects.

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A blood filtration system, comprising:
one or more sensors configured to determine one or more physiological parameters including venous oxygen saturation (SvO2) and hematocrit of a patient;
a controller in communication with the one or more sensors, wherein:
the controller is configured to monitor the physiological parameters using the sensors;
the controller includes a display module configured to generate content including a diagnostic matrix having a diagnostic point, and the display module is configured to change the diagnostic point within the diagnostic matrix according to changes in the monitored physiological parameters; and
the controller includes a therapy guidance module configured to determine a suggested corrective action based on the monitored physiological parameters, and the suggested corrective action is included in the content; and
a display configured for presenting the content.

2. The blood filtration system of claim 1, wherein:
the display module is configured to determine a zone of stability associated with the monitored physiological parameters; and
the zone of stability includes one or more value ranges for the physiological parameters.

3. The blood filtration system of claim 2, wherein the display is configured to present the diagnostic matrix and the zone of stability.

4. The blood filtration system of claim 1, wherein the display is configured to present the suggested corrective action, the diagnostic point, and a zone of stability.

5. The blood filtration system of claim 1, wherein the suggested corrective action includes changes in an extraction rate of filtrate fluid from blood of a patient.

6. The blood filtration system of claim 5, wherein the display is configured to display the suggested corrective action and the diagnostic matrix.

7. The blood filtration system of claim 1, wherein:
the therapy guidance module is configured to compare the monitored hematocrit with a hematocrit value range, the hematocrit value range extending between a first hematocrit value and a second hematocrit value;
the controller is configured to provide the suggested corrective action based on the comparison of the monitored hematocrit with the hematocrit value range.

8. The blood filtration system of claim 7, wherein:
the controller includes a comparator configured to compare the monitored SvO2 with a SvO2 value range, the SvO2 value range extending between a first SvO2 value and a second SvO2 value;
the controller is configured to provide the suggested corrective action based on the comparison of the monitored SvO2 with the SvO2 value range.

9. The blood filtration system of claim 8, wherein the suggested correction includes increasing a filtration rate when the hematocrit is within the hematocrit value range and the SvO2 is within the SvO2 value range.

10. The blood filtration system of claim 8, wherein the suggested correction includes decreasing a filtration rate when the hematocrit is outside the hematocrit value range and the SvO2 is within the SvO2 value range.

11. The blood filtration system of claim 8, wherein the suggested correction includes setting a filtration rate to zero when the hematocrit is outside the hematocrit value range and the SvO2 is outside the SvO2 value range.

12. The blood filtration system of claim 11, wherein the controller is configured to wait for a specified time period before providing the suggested correction.

13. The blood filtration system of claim 8, wherein the controller is configured to set a filtration rate to zero when the hematocrit is outside the hematocrit value range and the SvO2 is outside the SvO2 value range.

14. The blood filtration system of claim 8, wherein the controller is configured to set a filtration rate to zero when the hematocrit is outside the hematocrit value range and the SvO2 is outside the SvO2 value range.

15. The blood filtration system of claim 1, wherein the physiological parameters include one or more of relative blood volume, absolute blood volume, plasma volume, oxygen extraction ratio, ejection time, stroke volume, carotid flow time, cardiac output, cardiac power, central venous pressure, mean arterial pressure, systemic vascular resistance, heart rate, respiratory rate, cardiac power, hemoglobin concentration, extracellular fluid volume, or thoracic fluid content.

16. The blood filtration system of claim 15, wherein the controller includes an evaluation module configured to determine the physiological parameters using the one or more sensors.

17. The blood filtration system of claim 10, wherein the display module is configured to change a size of the diagnostic point in correspondence with changes in one or more of the monitored parameters.

18. The blood filtration system of claim 17, wherein the display module is configured to change a color of the diagnostic point in correspondence with changes in one or more of the monitored parameters.

19. The blood filtration system of claim 1, wherein the display module is configured to move the diagnostic point along one or more axis, the one or more axis corresponding with values of the monitored diagnostic parameters.

20. The blood filtration system of claim 1, wherein the physiological parameters comprise hemodynamic parameters that affect hemodynamic stability of the patient.

21. The blood filtration system of claim 1, wherein the controller is configured to determine a systemic vascular resistance (SVR) of the patient using the monitored physiological parameters.

22. The blood filtration system of claim 21, wherein:
the controller determines a first figure of merit corresponding to first basis of change in the SVR; and
the controller determines a second figure of merit corresponding to a second basis of change in the SVR.

23. The blood filtration system of claim 21, wherein:
the SVR equals a first quantity divided by a second quantity;
the first quantity equals a difference between a mean arterial pressure of a patient and a central venous pressure of the patient;
the second quantity equals a cardiac output of the patient.

* * * * *